United States Patent [19]
Yamashita et al.

[11] Patent Number: 5,974,857
[45] Date of Patent: Nov. 2, 1999

[54] APPARATUS AND METHOD FOR CONTROLLING OXYGEN SENSOR HEATING

[75] Inventors: Yukihiro Yamashita; Hisashi Iida; Jun Hasegawa, all of Kariya, Japan

[73] Assignee: Denso Corporation, Kariya, Japan

[21] Appl. No.: 09/172,662

[22] Filed: Oct. 15, 1998

Related U.S. Application Data

[62] Division of application No. 08/883,590, Jun. 26, 1997, Pat. No. 5,852,228.

[30] Foreign Application Priority Data

Jul. 10, 1996 [JP] Japan .................................... 8-180771
Apr. 23, 1997 [JP] Japan .................................... 9-105960

[51] Int. Cl.[6] .................................................. F02D 41/14
[52] U.S. Cl. ........................................................ 73/23.32
[58] Field of Search ................................ 73/118.1, 23.32; 123/694–697; 204/406

[56] References Cited

U.S. PATENT DOCUMENTS

| | | |
|---|---|---|
| 4,543,176 | 9/1985 | Harada et al. . |
| 5,524,472 | 6/1996 | Hotzel . |
| 5,544,640 | 8/1996 | Thomas et al. . |
| 5,709,198 | 1/1998 | Sagisaka et al. . |

FOREIGN PATENT DOCUMENTS

| | | |
|---|---|---|
| 61-122556 | 6/1986 | Japan . |
| 61-132851 | 6/1986 | Japan . |
| 63-140955 | 6/1988 | Japan . |
| 3-189350 | 8/1991 | Japan . |
| 3-189360 | 8/1991 | Japan . |

*Primary Examiner*—Robert Raevis
*Attorney, Agent, or Firm*—Nixon & Vanderhye P.C.

[57] ABSTRACT

A sensing element of an oxygen sensor is controlled to keep a target impedance for maintaining activation temperature of the oxygen sensor. As the sensing element deteriorates, its internal impedance increases and power supply to a heater for heating the sensing element increases. The oxygen sensor temperature rises excessively above an activation temperature. To restrict excessive temperature rise, the target impedance is altered when the supply power to the heater exceeds a predetermined reference. The target impedance may be increased with increase in the power supply to the heater. Alternatively, the heater supply power is limited to a predetermined maximum for restricting excessive temperature rise.

10 Claims, 15 Drawing Sheets

APPARATUS AND METHOD FOR CONTROLLING OXYGEN SENSOR HEATING

This is a division of application Ser. No. 08/883,590, filed Jun. 26, 1997, now U.S. Pat. No. 5,852,228.

BACKGROUND OF THE INVENTION

1. Field of the Invention

The present invention relates to an apparatus and method for controlling oxygen sensor heating to restrict sensor deterioration caused by excessive heating.

2. Description of Related Art

Many modern air-fuel ratio control systems for engines use a current limiting type oxygen sensor (oxygen concentration detector) which produces current proportional to oxygen concentration in exhaust gas.

This type of oxygen sensor is incapable of producing current proportional to the oxygen concentration until activated at predetermined temperature (activation temperature). Therefore, to maintain the activation of the oxygen sensor, power supply to a heater for heating the oxygen sensor is controlled in response to temperature of the sensing element in the oxygen sensor (element temperature feedback control).

The feedback control for the oxygen sensor temperature is based on the sensing element impedance which varies with temperature. The target impedance is set to the impedance at which the activation temperature is attained.

Internal impedance of the sensing element increases as the oxygen sensor deteriorates. Therefore, even when the temperature of the oxygen sensor is above the activation temperature, the supply power to the heater (heater supply power) will be increased to attain the target impedance because the impedance of the sensing element increases by deterioration. The temperature of the oxygen sensor will accordingly rise. Further, when the oxygen sensor operating characteristics change due to sensor deterioration or the sensor environment (e.g., engine exhaust gas temperature) changes, the heater supply power will become unstable and cause excessive heating of the sensing element. Thus, this temperature rise will adversely promote deterioration of the oxygen sensor.

SUMMARY OF THE INVENTION

It is an object of the present invention to obviate the foregoing drawbacks, while maintaining activation temperature of an oxygen sensor.

It is another object of the present invention to restrict temperature rise of an oxygen sensor which will occur when an oxygen sensor deteriorates and an internal impedance of a sensing element increases correspondingly.

According to the first aspect of the present invention, in an oxygen sensor heating apparatus and method which feedback-controls supply power to a heater, deterioration of an oxygen sensor is determined based on internal impedance of a sensing element, and target impedance is altered based on the deterioration determination result. Thus, even when the oxygen sensor deteriorates, the target impedance is increased to a new target impedance so that power supply to the heater is controlled to restrict temperature rise of the oxygen sensor.

Preferably, the deterioration is determined by comparing supply power to the heater with a determination reference, and the target impedance is altered when the supply power reaches the determination reference.

Preferably, abnormality of the oxygen sensor is determined to check whether the supply power to the heater corresponds to an operating limit of the oxygen sensor. Thus, when the supply power becomes large due to sensor deterioration, any further increase in the supply power is restricted.

Preferably, it is determined from engine operating state whether the increase in the supply power to the heater is caused by deterioration of the oxygen sensor or decrease in the exhaust gas temperature. Thus, the target impedance is altered when the engine runs in the steady state.

Preferably, the target impedance is altered increasingly as the supply power to the heater increases.

According to the second aspect of the present invention, the supply power to a heater is limited to a predetermined maximum supply power limit. This maximum limit restricts the excessive temperature rise of the oxygen sensor even when the heater supply power is likely to increase due to changes in sensor operating characteristics or sensor environment such as exhaust gas temperature.

Preferably, the maximum limit is set higher than normal for a predetermined period in which the oxygen sensor will uniformly heated, when the oxygen sensor is used from cold state.

Preferably, the maximum limit is set in accordance with the element impedance of the oxygen sensor.

BRIEF DESCRIPTION OF THE DRAWINGS

The foregoing and further objects, features and advantage of the present invention will become more apparent from the following description of preferred embodiments with reference to the accompanying drawings, wherein.

DETAILED DESCRIPTION OF PREFERRED EMBODIMENTS

Figure 1:
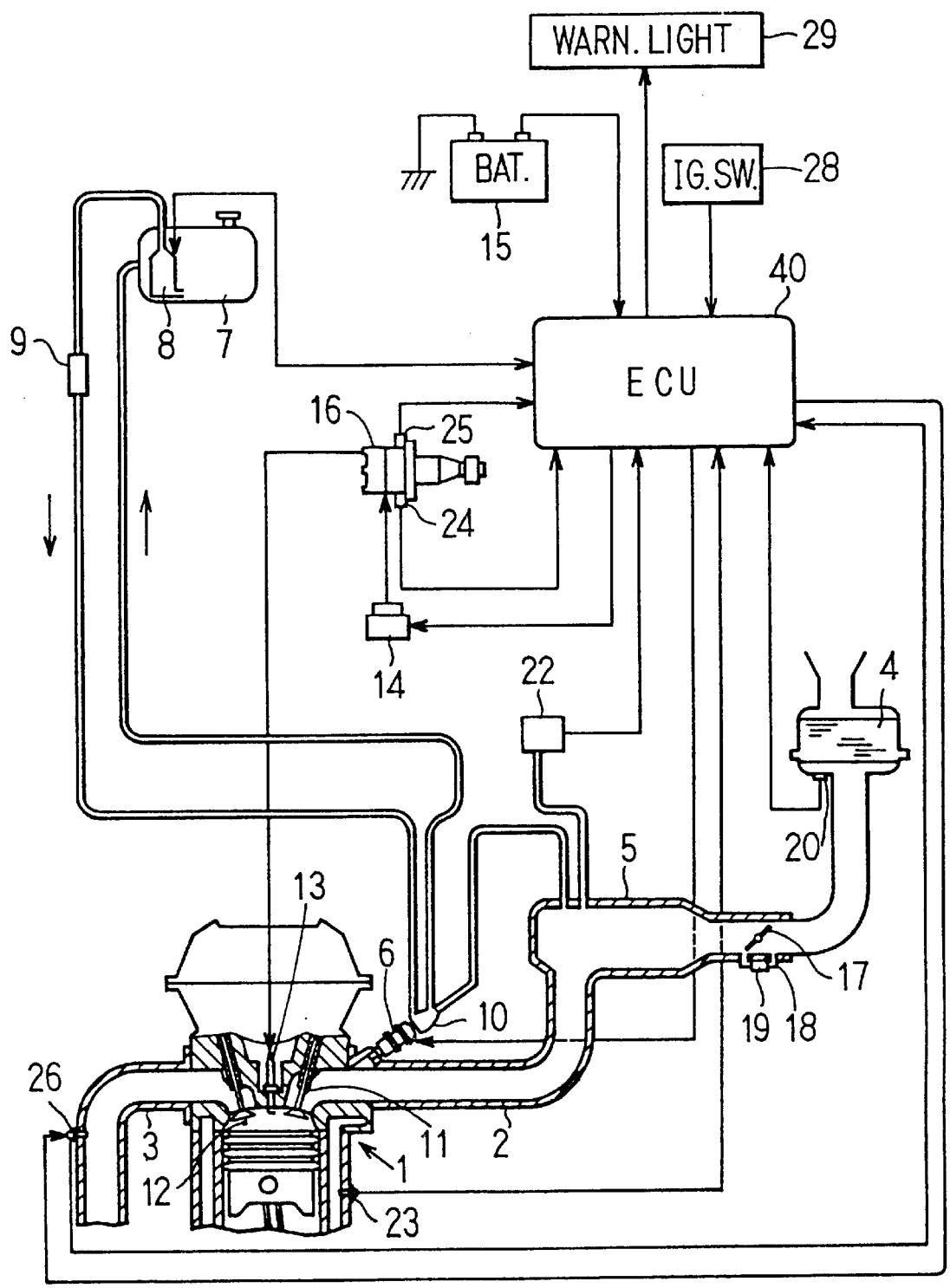
FIG. 1 is a schematic view of an air-fuel ratio control apparatus using oxygen sensor heating control according to the first embodiment of the present invention.

The present invention will be described with reference to two embodiments in which an oxygen sensor is used in an air-fuel ratio control apparatus for an automotive internal combustion engine. It is to be noted in the description to follow that the same or similar construction throughout the embodiments is denoted by the same or similar reference numerals to obviate repeated explanation.

First Embodiment

In FIG. 1 illustrating an air-fuel ratio control apparatus, a four-cylinder spark-ignition type gasoline internal combustion engine 1 is connected with an intake pipe 2 and an exhaust pipe 3. An air cleaner 4 is provided at the most upstream portion of the intake pipe 2. A surge tank 5 is provided halfway of the intake pipe 2. Disposed upstream from the surge tank 5 is a throttle valve 17 operable together with the depressing operation of an accelerator pedal (not shown). A bypass passage 18 bypassing the throttle valve 1 is provided with an ISC (idle speed control) valve 19.

The intake pipe 2 is connected to each cylinder of the engine 1 through an intake port on which an injector 6 is mounted. Fuel is pumped up from a fuel tank 7 by a fuel pump 8, and then supplied to a pressure regulator 10, via a fuel filter 9. The pressure regulator 10 is provided to regulate pressure of fuel to be supplied to the injector 6 by returning surplus fuel to the fuel tank 7. The injector 6 opens its valve to inject fuel by power supply from a battery 15. The fuel injected from the injector 6 is mixed with intake air to form air-fuel mixture. The mixture is then introduced into a combustion chamber 12 by an intake valve 11.

An intake air temperature sensor 20 is disposed near the air cleaner 4 to detect the temperature of intake air. The surge tank 5 is connected with a pressure sensor 22 for detecting the intake air pressure inside the intake pipe 2. The cylinder block of the engine 1 is provided with a temperature sensor for detecting the temperature of the engine coolant.

A spark plug 13 is mounted on the combustion chamber 12 of each cylinder. An igniter 14 generates a high voltage from the voltage supplied from the battery 15. The high voltage is then distributed to the spark plug 13 of each cylinder by a distributor 16. The distributor 16 includes a reference position sensor 24 for detecting a reference rotational position and a crank angle sensor 25. The crank angle sensor 25 generates crank angle signals at every predetermined crank angles (for example, at every 30° CA) during rotation of the crankshaft of the engine 1. The reference position sensor 24 generates a reference position signal with respect to a specific cylinder (for example, the compression top dead center position of the first cylinder) during rotation of the crankshaft of the engine 1, thereby detecting the cylinder number.

The exhaust pipe 3 of the engine 1 is provided with a current limiting type oxygen sensor 26 that outputs detection signals linear with (proportional to) the oxygen concentration in exhaust gas. Disposed downstream from the oxygen sensor 26 is a catalyst converter (not shown) that cleans exhaust gas.

The detection signals from the aforementioned sensors are inputted to an electronic control unit (ECU) 40. The ECU 40 operates on the power supply from the battery 15. Upon receiving an ON-signal from an ignition switch 28, the ECU 40 starts controlling operation of the engine 1. During operation of the engine 1, the ECU 40 feedback-controls the air-fuel ratio of air-fuel mixture to approximately a target air-fuel ratio (for example, the stoichiometric air-fuel ratio) by altering the air-fuel ratio correction coefficient on the basis of the signals from the oxygen sensor 26. Furthermore, the ECU 40 performs oxygen sensor diagnosis operation, i.e., oxygen sensor malfunction determination operation, to determine whether abnormality has occurred in the oxygen sensor 26, and when abnormality has occurred, turns on a warning light 29 to inform the driver of the oxygen sensor abnormality.

Figure 2:
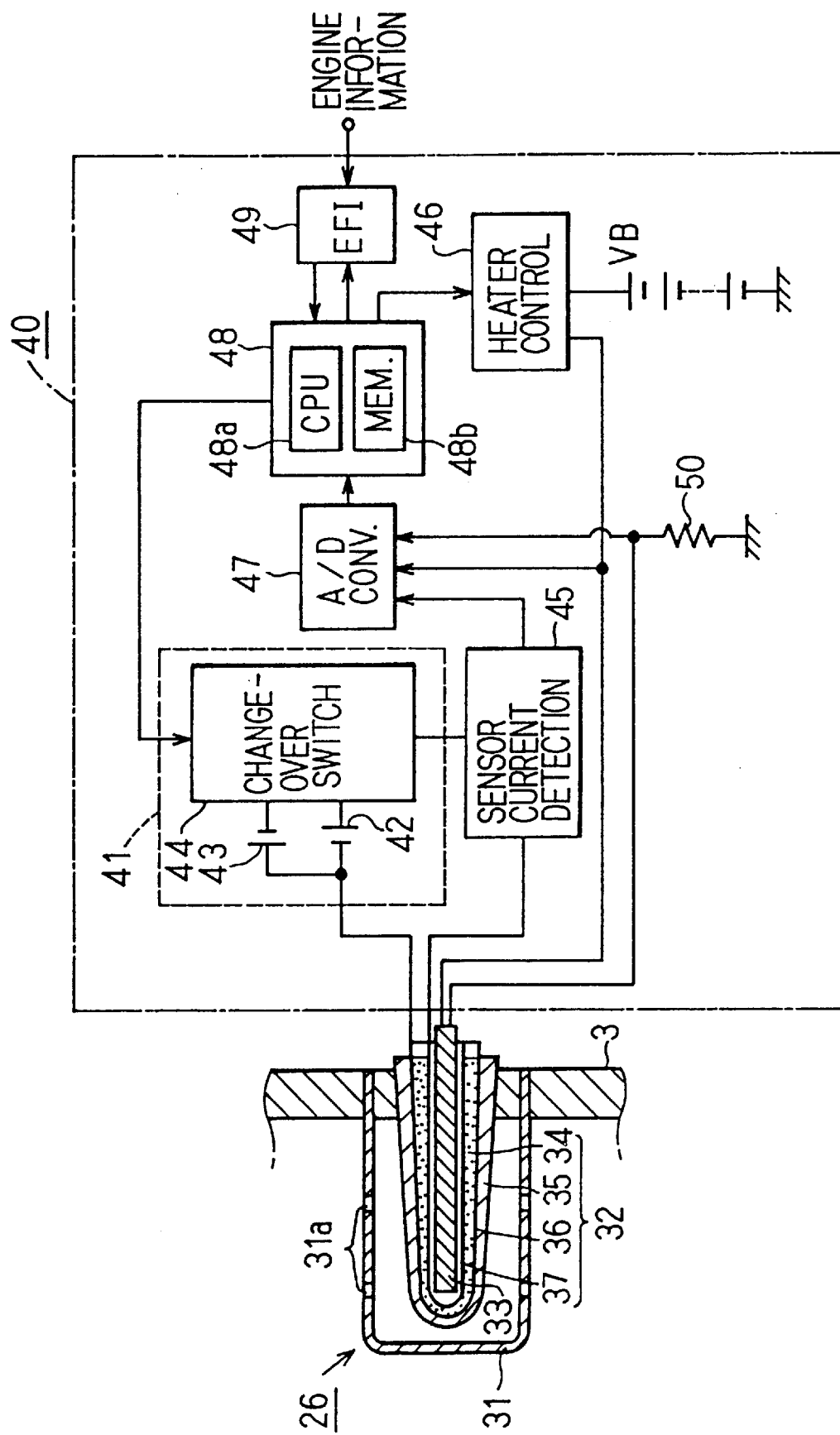
FIG. 2 is a sectional view of an oxygen sensor and an electric circuit diagram of an ECU.

As shown in FIG. 2, the oxygen sensor 26 is projected into the exhaust pipe 3. It comprises a cover 31, a sensor body 32 and a heater 33. The cover 31 has a generally "U" sectional shape, and its peripheral wall has many pores 31a that communicate the inside of the cover 31 and the outside. The sensor body 32 produces limit current corresponding to the oxygen concentration in the lean mixture region of the air-fuel ratio or the concentration of carbon monoxide (CO) in the rich mixture region of the air-fuel ratio.

An exhaust gas-side electrode layer 36 is fixed onto the outer surface of a solid electrolyte layer 34 having a sectional shape of a cup. The inner surface of the solid electrolyte layer 34 is fixed to the atmosphere-side electrode layer 37. A diffused resistance layer 35 is formed on the outside of the exhaust gas-side electrode layer 36 by plasma spraying or the like.

The heater 33 is disposed in a space surrounded by the atmosphere-side electrode layer 37. The thermal energy from the heater 33 heats the sensor body 32 (the atmosphere-side electrode layer 37, the solid electrolyte layer 34, the exhaust gas-side electrode layer 36 and the diffused resistance layer 35). The heater 33 has a sufficient heat generating capacity to activate the sensor body 32.

With this construction of the oxygen sensor 26, the sensor body 32 generates variable electromotive force at the stoichiometric air-fuel ratio, and produces limit current in accordance with the oxygen concentration within the lean mixture region defined with respect to the stoichiometric air-fuel ratio.

The sensor body 32 linearly detects the oxygen concentration in the exhaust gas. However, since high temperature of about 650° C. or higher is needed to activate the sensor body 32 and the activation temperature range of the sensor body 32 is relatively narrow, the thermal energy from exhaust gas from the engine 1 is not sufficient to control the activation of the sensor body 32. According to this embodiment, the heater 33 is controlled as described later so as to achieve desired control of the temperature of the sensor body 32. Within a rich mixture region with respect to the stoichiometric air-fuel ratio, on the other hand, the concentration of carbon monoxide (CO), that is, an unburned gas, varies substantially linearly with the air-fuel ratio. The first sensor body 32 generates limit current in accordance with the CO concentration in the rich mixture region.

Figure 3:
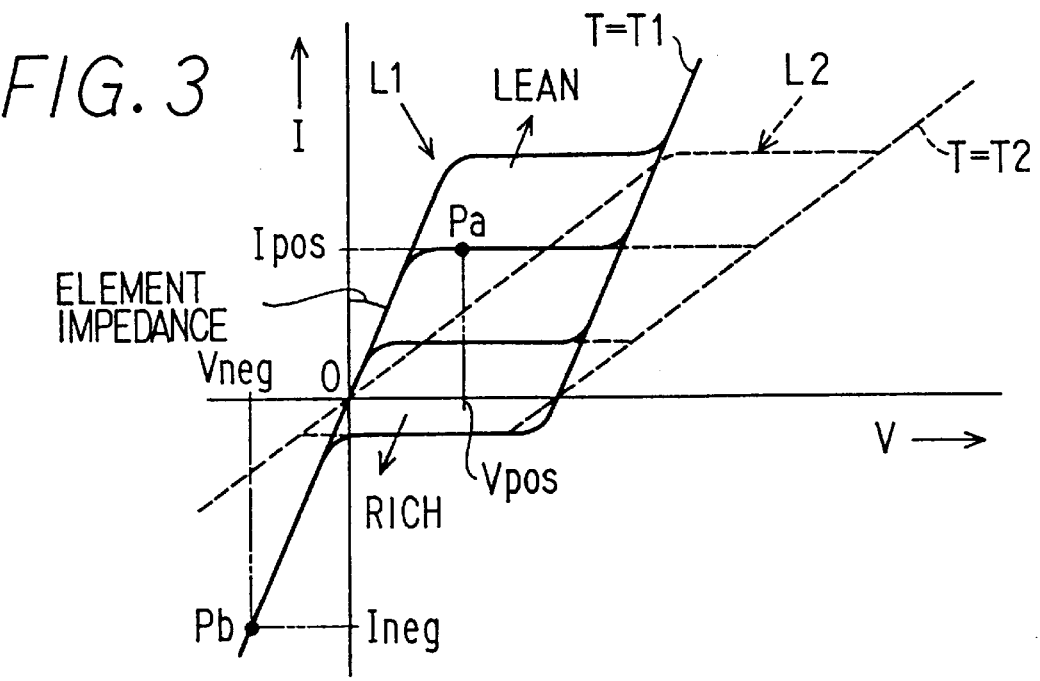
FIG. 3 is a graph indicating the voltage-current characteristics of the oxygen sensor.

The current-voltage characteristic curves in FIG. 3 indicate that the current flowing into the solid electrolyte layer 34 of the sensor body 32 in proportion to the oxygen concentration (air-fuel ratio) detected by the oxygen sensor 26 is linear with the voltage applied to the solid electrolyte layer 34.

When the sensor body 32 is in the activated state at a temperature T=T1, the current-voltage characteristics of the sensor body 32 exhibit a stable state as indicated by characteristic curve L1 represented by solid lines in FIG. 3. The straight segments of the characteristic curve L1 parallel to the voltage axis V specify limit currents which flows in the sensor body 32. The variation of the limit current accords with the variation of the air-fuel ratio (that is, lean or rich). More precisely, the limit current increases as the air-fuel ratio shifts further to the lean side, and the limit current decreases as the air-fuel ratio shifts further to the rich side.

The region of the voltage-current characteristic curve where the voltage is smaller than the levels corresponding to the straight segments parallel to the voltage axis V is a resistance-dominant region. The slope of the characteristic curve L1 within such resistance-dominant region is determined by the internal impedance (element impedance) of the solid electrolyte layer 34 provided in the sensor body 32. The element impedance varies with temperature. As the temperature of the sensor body 32 decreases, the element impedance increases and, therefore, the slope is reduced.

When the temperature T of the sensor body 32 is T2 that is lower than T1, the current-voltage characteristics of the sensor body 32 become as indicated by the characteristic curve L2 represented by broken lines in FIG. 3. The straight segments of the characteristic curve L2 parallel to the voltage axis V specify limit currents which flows in the sensor body 32. The limit currents determined by the characteristic curve L2 are substantially equal to those determined by the curve L1.

With the characteristic curve L1, if a positive voltage Vpos is applied to the solid electrolyte layer 34 of the sensor body 32, the current flowing through the sensor body 32 becomes a limit current Ipos (see point Pa in FIG. 3). If a negative voltage Vneg is applied to the solid electrolyte layer 34 of the sensor body 32, the current through the sensor body 32 becomes a negative limit current Ineg that is not dependent on the oxygen concentration but proportional solely to the temperature (see point Pb in FIG. 3).

Referring again to FIG. 2, the exhaust gas-side electrode layer 36 of the sensor body 32 is connected to a bias control circuit 41 that is connected to the atmosphere-side electrode layer 37 of the sensor body 32 via a positive bias DC power source 42. The bias control circuit 41 is generally composed of the positive bias DC power source 42, a negative bias DC power source 43 and a change-over switch circuit 44. The negative electrode of the positive bias DC power source 42 and the positive electrode of the negative bias DC power source 43 are connected to the exhaust gas-side electrode layer 36.

The change-over switch circuit 44 selectively connects only the positive electrode of the positive bias DC power source 42 to a sensor current detecting circuit 45 when switched to a first selection state. When switched to a second selection state, the change-over switch circuit 44 connects only the negative electrode of the negative bias DC power source 43 to the sensor current detecting circuit 45. That is, when the change-over switch circuit 44 is in the first selection state, the positive bias DC power source 42 positively biases the solid electrolyte layer 34 of the sensor body 32 so that current flows through the solid electrolyte layer 34 in the positive direction.

On the other hand, when the change-over switch circuit 44 is in the second selection state, the negative bias DC power source 43 negatively biases the solid electrolyte layer 34 so that current flows through the solid electrolyte layer 34 in the negative direction. The terminal voltages of the positive and negative bias DC power sources 42, 43 correspond to the aforementioned applied voltages Vpos and Vneg, respectively.

The sensor current detecting circuit 45 detects the current flowing from the atmosphere-side electrode layer 37 of the sensor body 32 to the switch circuit 44 or in the reversed direction, that is, the current flowing through the solid electrolyte layer 34. A heater control circuit 46 duty-controls the electric power supplied from a battery power source VB to the heater 33 in accordance with the heater temperature and/or the element temperature of the oxygen sensor 26, thus controlling the heating by the heater 33. The current flowing through the heater 33 (heater current Ih) is detected by a current detecting resistor 50.

An A/D converter 47 converts the current detected by the sensor current detecting circuit 45 (Ipos, Ineg indicated in FIG. 3), the heater current Ih, and the voltage applied to the heater 33 (heater voltage Vh) into corresponding digital signals, and outputs the signals to a microcomputer 48. The microcomputer 48 comprises a CPU 48a for executing various calculation operations, and a memory 48b composed of a ROM and a RAM. In accordance with prestored computer programs, the microcomputer 48 controls the bias control circuit 41, the heater control circuit 46, an electronic fuel injection control apparatus (EFI) 49 and the like. The fuel injection control apparatus 49 receives various signals from the aforementioned sensors as engine information and thereby detects intake air temperature Tam, intake negative pressure Pm, coolant temperature Thw, engine speed NE, vehicle speed Vs and the like. Based on such engine information, the fuel injection control apparatus 49 controls fuel injection performed by the injector 6.

The operation of this embodiment will be described with reference to the control programs executed by of the CPU 48a of the microcomputer 48.

Figure 4:
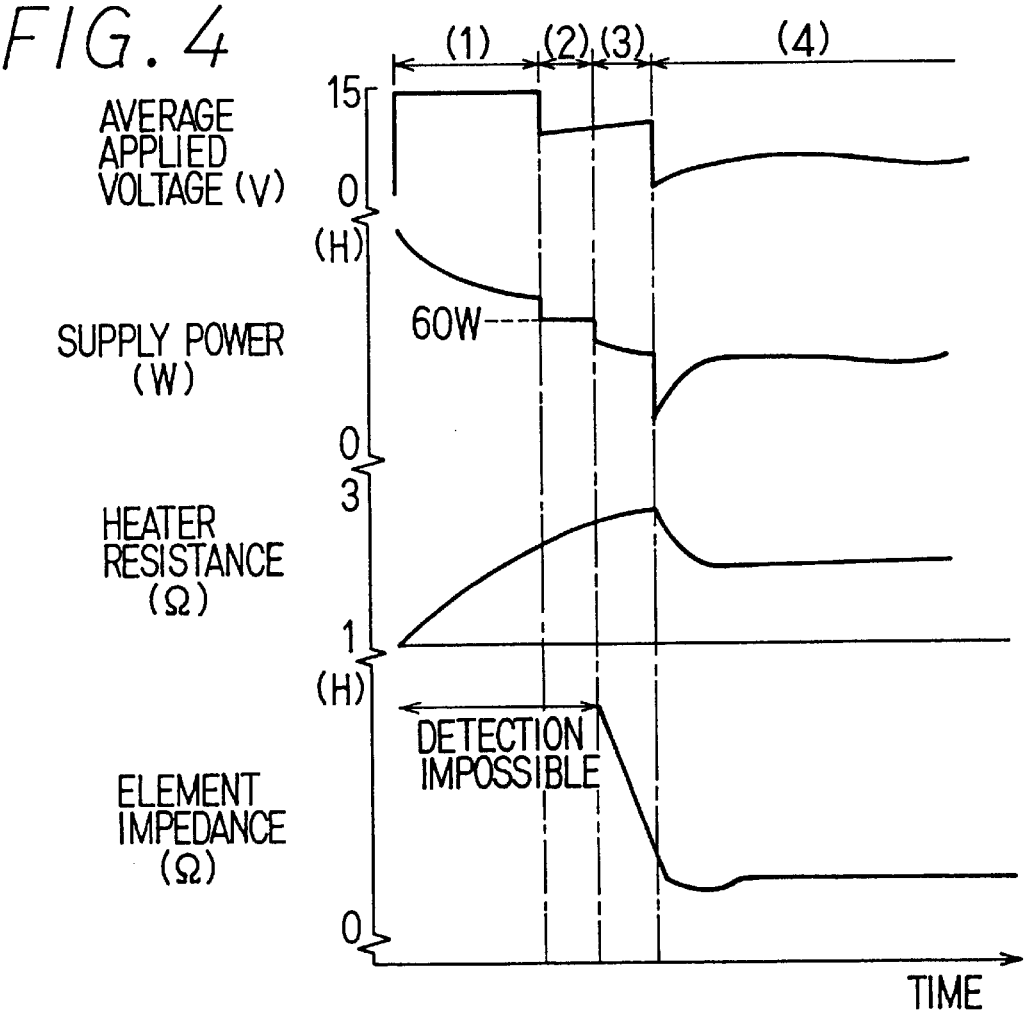
FIG. 4 is a time chart illustrating heater supply power control operation.

FIG. 4 shows a timing chart indicating heater control performed from the starting of power supply to the heater 33 in response to the starting of the engine 1 until sufficient activation of the oxygen sensor 26. According to this embodiment, the heater control can be divided into four modes (1)–(4) in view of the different purposes and control methods. These control modes will be described in sequence. The control modes (1)–(3) are performed to control the heater 33 before the oxygen sensor 26 is activated, and the control mode (4) is performed to control the heater 33 after the oxygen sensor 26 has been activated.

Figure 5:
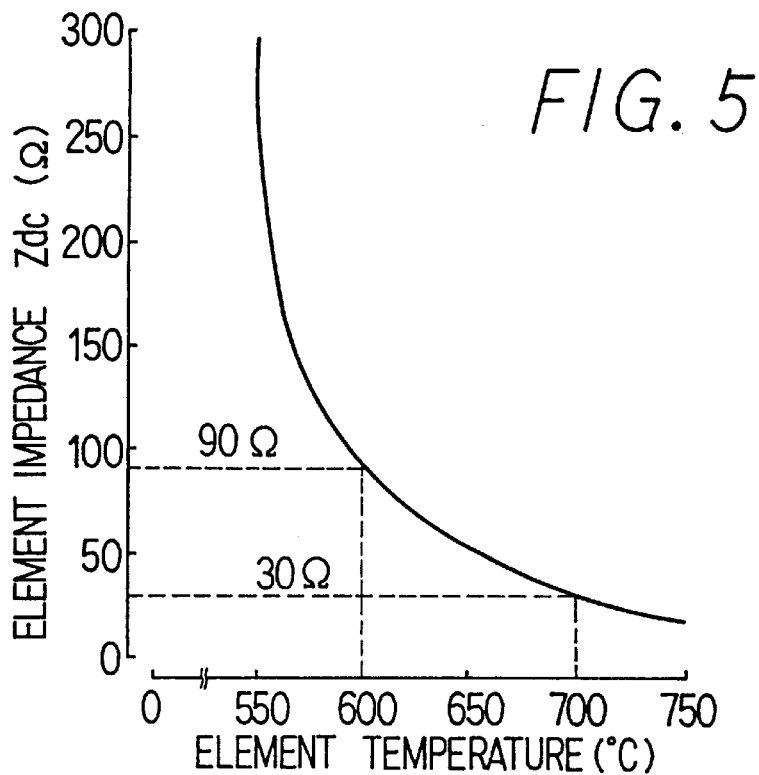
FIG. 5 is a graph indicating the relation between element temperature and element impedance of an oxygen sensing element in the oxygen sensor.

In the control mode (1) performed immediately after the starting of the engine 1, the 100% duty heater voltage is applied to the heater 33. This control will be referred to as "full energization control". That is, the maximum voltage is supplied to the heater 33 to quickly heat the heater 33 when the heater 33 and the sensor element of the sensor body 32 are cold. The control modes (2) and (3) control the power supply to the heater 33 to maintain the heater temperature at a target heater temperature (for example, 1200° C. which is the upper limit heater temperature). Hereinafter, these control modes will be referred to as "power control". Since the heater temperature is specifically determined by the supply power to the heater 33 if the element temperature is substantially the activation temperature (700° C.), the temperature of the heater 33 can be maintained at a constant level by continuing to supply a predetermined power. However, if the element temperature is low, the power supply needed to maintain the heater temperature at a constant level varies with the element temperature. Normally, as the element temperature is lower, the power supply required is larger. During the power control, the power supply to the heater 33 is controlled in accordance with the element impedance having relation with the element temperature as indicated in FIG. 5.

However, in an initial period of the power control, the element impedance is considerably large, that is, it exceeds the maximum detectable value (for example, 600Ω). In such an element impedance undetectable region, the power supply to the hater 33 is maintained at a constant level (for example, 60W) (control mode (2)). When the element temperature is increased so that the element impedance becomes 600Ω or lower, the power in accordance with the element impedance is then supplied to the heater 33 (control mode (3)).

The control mode (4) feedback-controls the power supply to the heater 33 to achieve a target impedance (corresponding to a target temperature) in order to maintain the activation of the sensor element (hereinafter, referred to as "element temperature feedback control"). As long as the oxygen sensor 26 is normal and not deteriorated, the power supply is controlled so that the element impedance attains the target value 30Ω (target temperature 700° C.).

Figure 6:
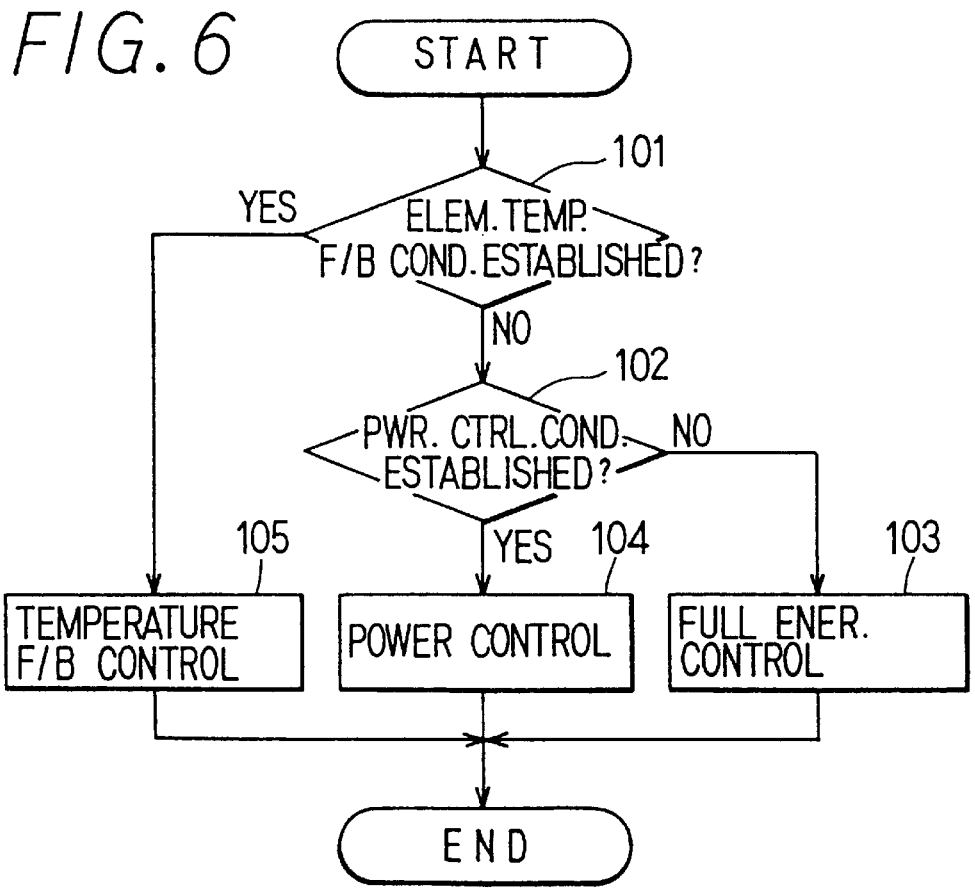
FIG. 6 is a flowchart illustrating a heater supply power control routine.

A heater control routine according to the embodiment will be described with reference to FIG. 6. In FIG. 6, the CPU 48a determines in step 101 whether the precondition for the element temperature feedback control have been established. The precondition is satisfied if the element impedance of the oxygen sensor 26 is equal to or less than 30Ω. The CPU 48a determines in step 102 whether the preconditions for the power control have been established.

Two different preconditions have been arranged separately in accordance with whether the oxygen sensor 26 (the sensor body 32 and the heater 33) is in a cold state or not. If the oxygen sensor 26 is in the cold state, the precondition is satisfied when a predetermined length of time has elapsed following the starting of the full energization control (the control mode (1) indicated in FIG. 4). If the oxygen sensor 26 is no longer in the cold state, the precondition is satisfied when the heater resistance has reached or exceeded a target heater resistance. By executing the full energization control selectively when the oxygen sensor 26 is in the cold state, an excessive rise of the heater temperature can be prevented when the engine 1 is restarted after a short stop.

If both step 101 and step 102 make negative determination (NO) in an initial period of the heater control, the CPU 48a proceeds to step 103 to execute the full energization control of the heater 33 (control mode (1)). That is, the 100% duty heater voltage is applied to the heater 33.

If the preconditions for the power control are satisfied (YES) in step 102, the CPU 48a proceeds to step 104 to execute the power control (control modes (2), (3)). As described above, if the element impedance is in the undetectable range (element impedance>600Ω), the power supply to the heater 33 is controlled to a fixed value (control mode (2)). If the element impedance becomes detectable, the power supply to the heater 33 is controlled in accordance with the element impedance to maintain the heater temperature to a target heater temperature (control mode (3)).

If the precondition for the element temperature feedback control is satisfied in step 101 in a later period, the CPU 48a proceeds to step 105 to execute the element temperature feedback control (control mode (4)). For this control, the CPU 48a computes a heater control duty DUTY based on the following equations:

$$DUTY = DUTY.I + GP + GI$$

$$GP = KP \cdot (Zdc - ZdcT)$$

$$GI = GI + KI \cdot (Zdc - ZdcT)$$

where DUTY.I is an initial value of the control duty DUTY; Zdc is an element impedance; and ZdcT is a target impedance. According to this embodiment, DUTY.I is set to 20%, ZdcT is set to 30Ω. GP is a proportional term; GI is an integral term; KP is a proportion constant; and KI is an integration constant (according to this embodiment, KP=4.2%, KI=0.2%). These values can be experimentally determined, and will alter in accordance with the specifications of the oxygen sensor 26.

Figure 7:
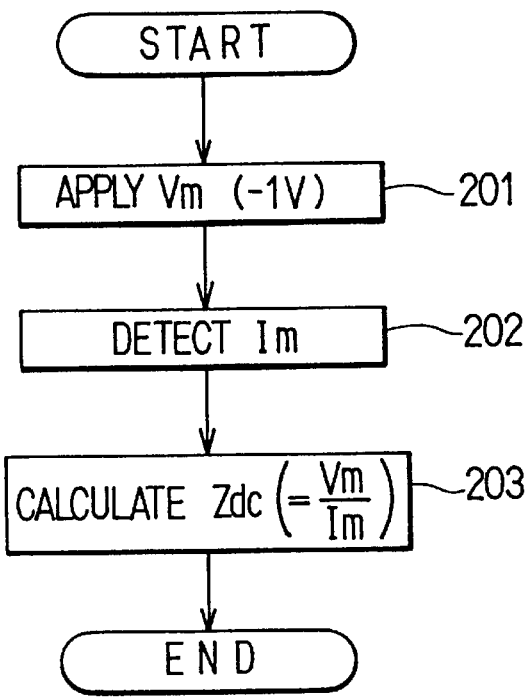
FIG. 7 is a flowchart illustrating an element impedance detection control routine.
Figure 8:
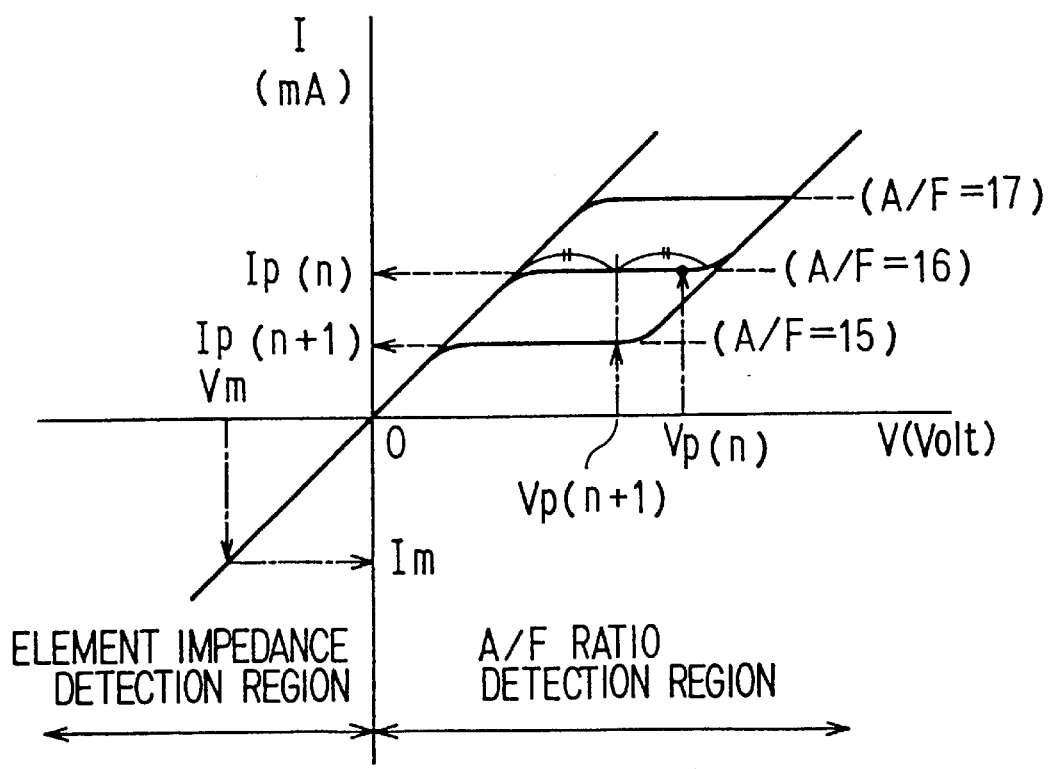
FIG. 8 is a graph illustrating the voltage-current characteristics of the oxygen sensor.

In FIG. 7 illustrating an element impedance detection routine performed during the element temperature feedback control (step 105 in FIG. 6), the CPU 48a applies in step 201 a predetermined voltage Vm (for example, −1V) in the element impedance detection region in FIG. 8, and reads at the subsequent step 202 the current Im detected by the sensor current detection circuit of FIG. 2. The CPU 48a then calculates in step 203 the element impedance Zdc (Zdc=Vm/Im) from the applied voltage Vm and the detected current Im.

Figure 9:
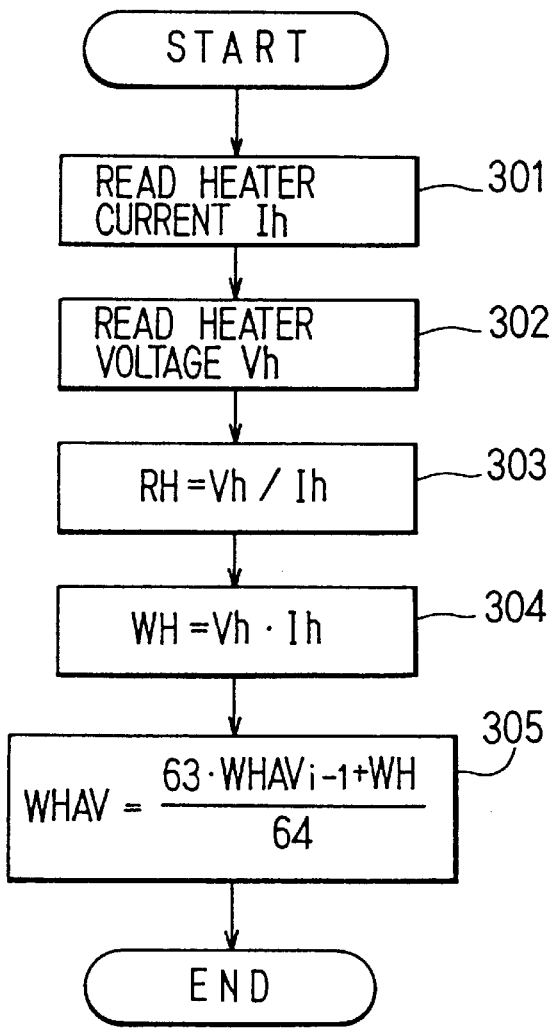
FIG. 9 is a flowchart illustrating a heater supply power average calculating routine.

In the flowchart of FIG. 9 illustrating a processed data calculating routine executed by CPU 48a, for example, in a cycle of 128 ms, the CPU 48a reads in step 301 the heater current Ih detected by the current detecting resistor 50 shown in FIG. 2, and reads in at the subsequent step 302 the heater voltage Vh.

The CPU 48a then calculates a heater resistance RH by dividing the heater voltage Vh by the heater current Ih (RH=Vh/Ih) in step 703, and multiplies in step 304 the heater voltage Vh by the heater current Ih to determine the heater supply power WH (WH=Vh·Ih). Then, the CPU 48a calculates a weighted average (hereinafter, referred to as "power average WHAV") of the heater supply power WH by 1/64-weighted average calculation using the following equation:

$$WHAV = (63 \cdot WHAVi-1 + WH)/64\}$$

Figure 10:
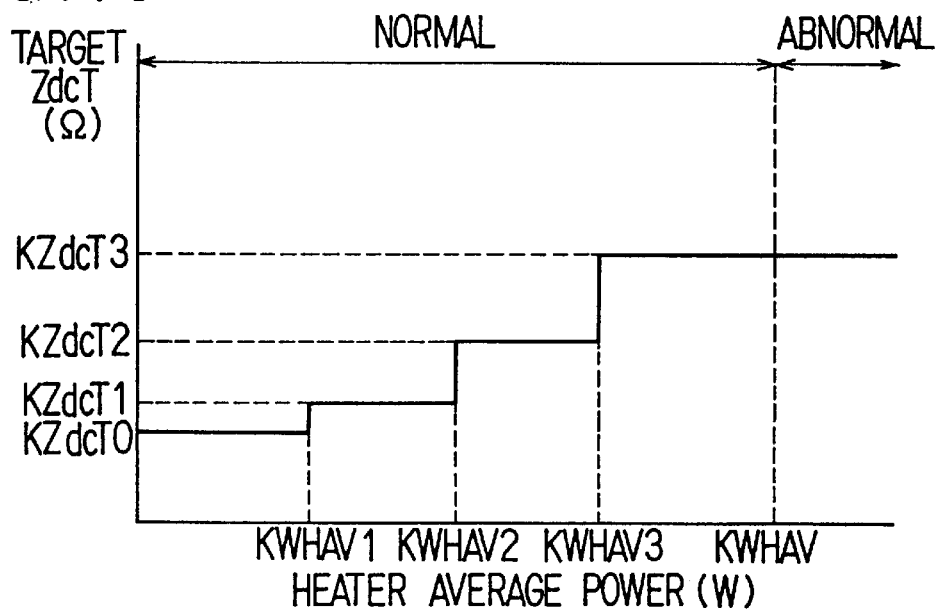
FIG. 10 is a flowchart illustrating the relation between the heater supply power average and the target impedance.

The target impedance is altered as shown in FIG. 10. As long as the oxygen sensor 26 is not deteriorated, the target impedance is set to 30. As the oxygen sensor 26 deteriorates, the impedance increases correspondingly and the heater supply power increases.

The heater supply power required to maintain the target impedance is generally corresponds to a predetermined electric power. Therefore, if the supply power exceeds the predetermined power, the oxygen sensor 26 may be determined to have deteriorated and the target impedance may be altered in accordance with the deterioration.

As shown in FIG. 10, KZdcT0 (30Ω) is set as the target impedance until deterioration occurs. After the occurrence of the deterioration, the target impedance is altered to KZdcT1 as long as the heater supply power is equal to or more than KWHAV1 and less than KWHAV2. Further, it is altered to KZdcT2 as long as the heater power supply is equal to or more than KWHAV2 and less than KWHAV3, and to KZdcT3 as long as the heater power supply is equal to or more than KWHAV3. Here, as shown in the figure, the heater supply power and the target impedance are set as KWHAV1<KWHAV2<KWHAV3<KWHAV and KZdcT0<KZdcT1<KZdcT2<KZdcT3.

When the heater supply power increases further and enters into the abnormality determination region (the supply power is above KWHAV), it is determined that the oxygen sensor 26 is abnormal. That is, because the air-fuel ratio detecting region is narrowed as the target impedance increases, the oxygen sensor 26 is determined to be abnormal when the detection ability of the oxygen sensor 26 reaches its limit.

Figure 11:
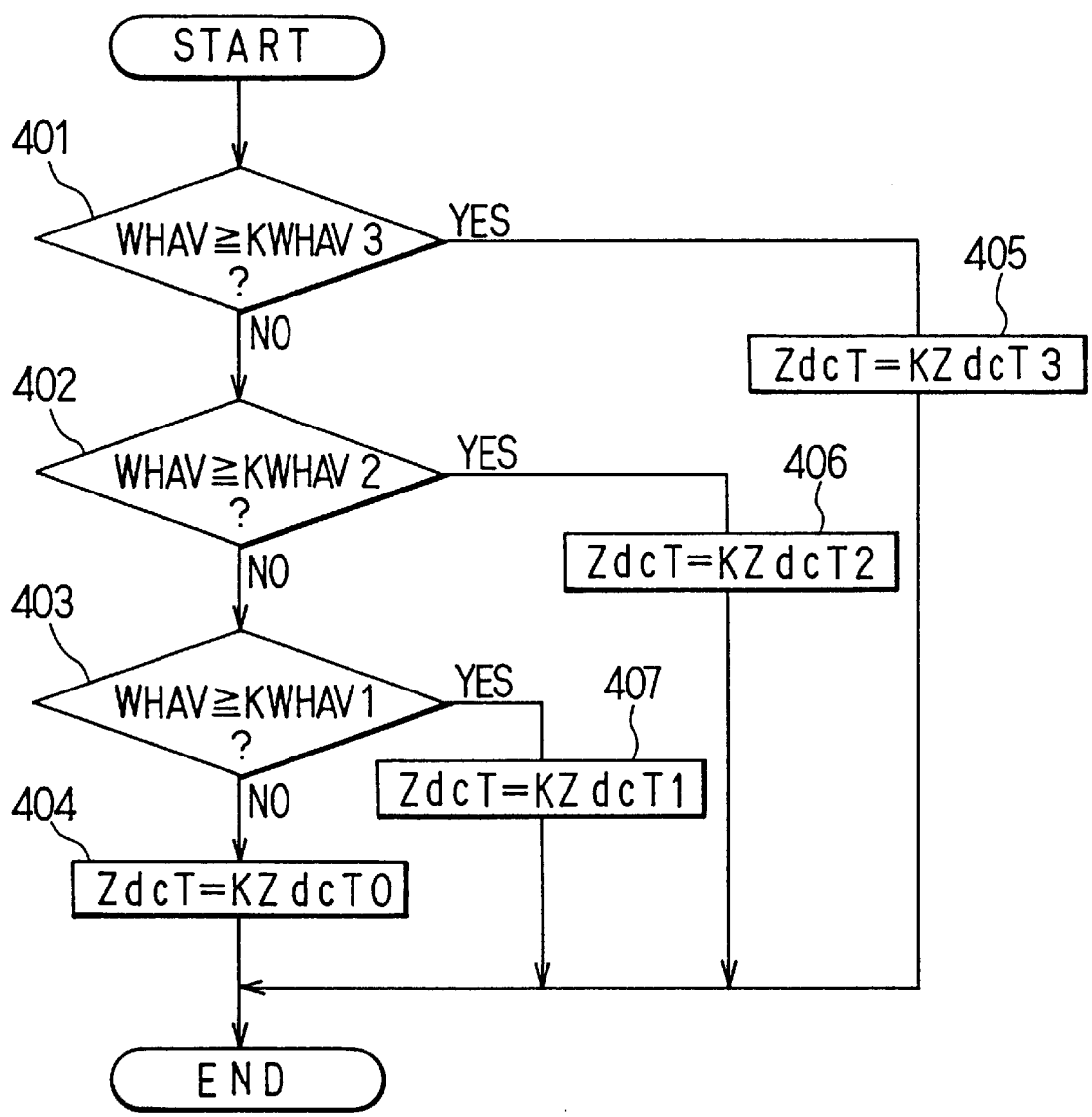
FIGS. 11 is a flowchart illustrating a target impedance altering routine.

FIG. 11 illustrates a flow chart of a target impedance altering routine which performs operation of FIG. 10. This flow chart corresponds to a step 505 shown in FIG. 12 which will be described later.

The CPU 48a determines in step 401 whether the power average WHAV is equal to or more than KWHAV3 (WHAV≧KWHAV3). If WHAV<KWHAV3, the CPU 48a proceeds to step 402 and determines whether the power average WHAV is equal to or more than KWHAV2 (WHAV≧KWHAV2). If WHAV<KWHAV2, the CPU 48a proceeds to step 403 and determines whether the power average KWHAV is equal to or more than KWHAV1 (WHAV≧KWHAV1). If WHAV<KWHAV1, the CPU 48a proceeds to step 404 and set the target impedance ZdcT to KZdcT0, thereby ending the routine.

If WHAV≧KWHAV1 in step 403, the CPU 48a proceeds to step 407 and sets the target impedance ZdcT to KZdcT1, thereby ending the routine. If WHAV≧KWHAV2 in step 402, the CPU 48a proceeds to step 406 and sets the target impedance ZdcT to KZdcT2, thereby ending the routine. If WHAV≧KWHAV1 in step 401, the CPU 48a proceeds to step 405 and sets the target impedance ZdcT to KZdcT3, thereby ending the routine.

As described above, the target impedance is altered in accordance with the degradation of the oxygen sensor 26 from the relations, i.e., KWHAV1<KWHAV2<KWHAV3<KWHAV and KZdcT0<KZdcT1<KZdcT2<KZdcT3.

Figure 12:
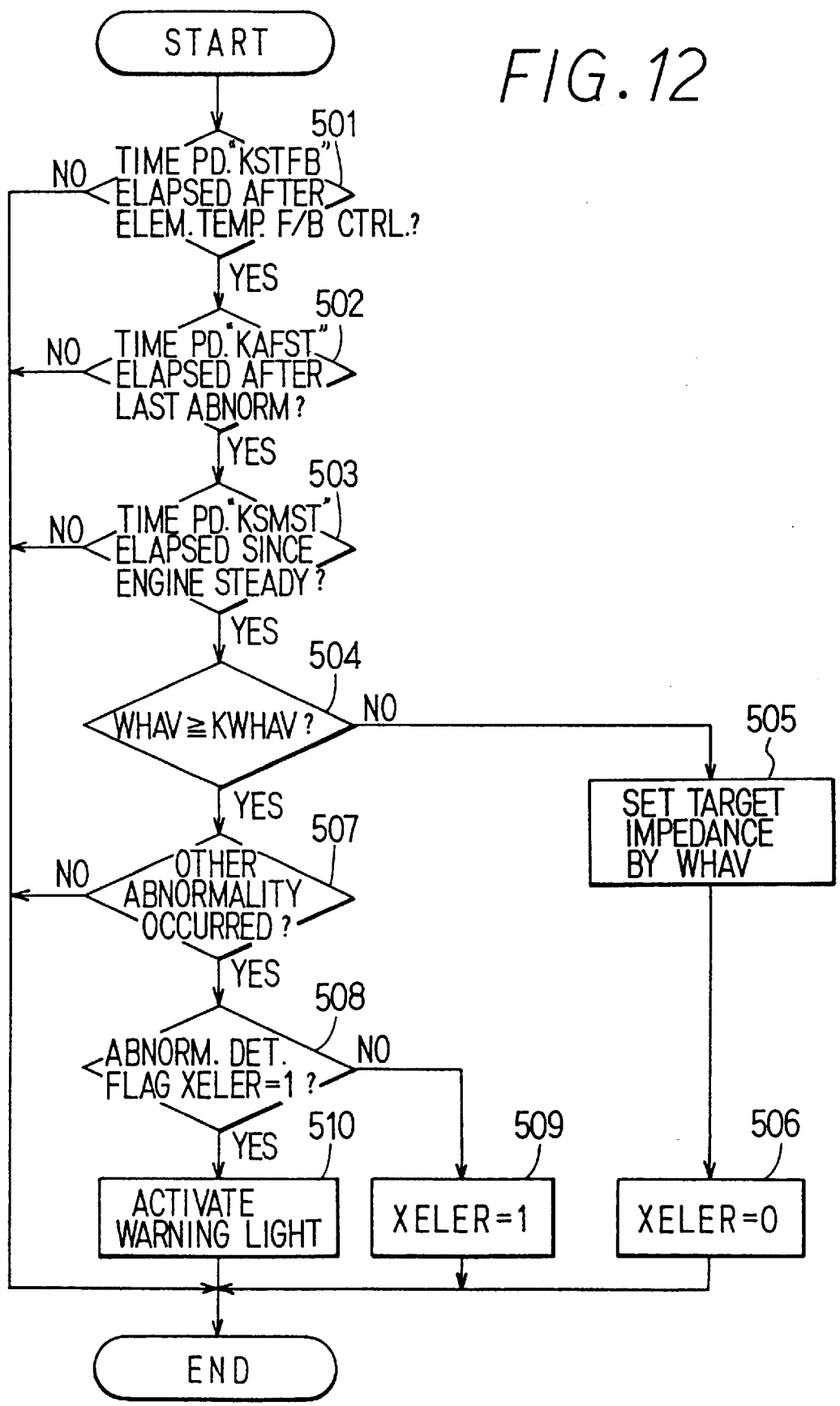
FIG. 12 is a flowchart illustrating sensor abnormality determination routine.

The flowchart of FIG. 12 illustrates a sensor diagnosis or abnormality detecting routine executed by the CPU 48a, for example, in a cycle of 1 second. The sensor diagnosis routine checks for sensor abnormality on the basis of the heater power supply WH needed during execution of the element temperature feedback control. More specifically, since the heater power supply WH needed to maintain the element temperature at a target value (for example, 700° C.) increases if the oxygen sensor 26 has abnormality, the sensor abnormality can be easily determined by comparing that heater power supply WH with the normal value. The procedure of the diagnosis will be described with reference to FIG. 12.

In step 501 in FIG. 12, the CPU 48a determines whether a predetermined length of time KSTFB (for example, 10 seconds) has elapsed following the start of the element temperature feedback control. Step 502 determines whether a predetermined length of time KAFST (for example, 100 seconds) has elapsed following the last determination of abnormality. Further, step 503 determines whether a steady engine operating state (for example, the idling state) has continued for a predetermined length of time KSMST (for example, 5 seconds). If any of steps 501–503 makes negative determination, the CPU 48a immediately ends this routine. If all of steps 501–503 make affirmative determination, the CPU 48a proceeds to step 504.

The CPU 48a determines in step 504 whether the power average WHAV equals or exceeds a predetermined heater power criterion KWHAV (whether WHAV≧KWHAV). If WHAV<KWHAV, it is considered that no sensor abnormality has occurred. The CPU 48a, determining no sensor abnormality, then proceeds to step 505 and alter the target impedance in accordance with WHAV. The above-described value ZdcT becomes the altered target impedance at this moment. The CPU 48a proceeds to step 506 to clear an abnormality determination flag XELER to "0", and then ends the routine.

On the other hand, if WHAV≧KWHAV, then the CPU 48a proceeds to step 507 to determine whether any abnormality other than sensor abnormality has been detected. If no such abnormality has been detected, the CPU 48a proceeds to step 508 to determine whether the abnormality determination flag XELER has been set to "1". If ZELER=0, then the CPU 48a sets the abnormality determination flag ZELER to 1 in step 509.

If ZELER=1, the CPU 48a proceeds to step 510 to turn on the warning light 29 to indicate the occurrence of abnormality as a diagnosis indicating procedure. In the operation through steps 504–510, if occurrence of abnormality (WHAV≧KWHAV) is determined successively twice, the diagnosis procedure is then executed.

As described above, according to the present embodiment, it is determined in step 503 whether the engine is in the steady operating state. The determination of the steady operating state is made based on the engine rotation speed NE and the engine load (intake negative pressure Pm or the like) detected by the fuel injection control apparatus 49.

Detection of the operating state is made for determining the exhaust gas temperature. More specifically, it is based on the fact that the heater supply power rises above the predetermined range in response to increase in the element impedance caused by sensor degradation or in response to decrease in the exhaust gas temperature. That is, the oxygen sensor 26 will become sufficiently activated even when the heater supply power is low, as long as the exhaust gas temperature is high. However, it will not become activated unless the heater supply power is high, when the exhaust gas temperature is low. Therefore, the heater needs high supply power when the exhaust gas temperature is low. Thus, the heater supply power under this state must be distinguished.

In the present embodiment, as long as the oxygen sensor 26 is not deteriorated, the supply power to the heater 33 is feedback-controlled (element temperature feedback control in FIG. 6) so that the element impedance (element temperature) of the oxygen sensor 26 becomes the target impedance 30Ω (target temperature 700° C.).

When the oxygen sensor 26 deteriorate, the target impedance is altered in accordance with its deterioration. During this process, the sensor is determined to be abnormal if the heater supply power exceeds the heater power determination level, and warning indication is provided by turning on the warning light 29.

Thus, the target impedance which varies with increase in the internal impedance of the element 34 is altered to a new target impedance, so that excessive temperature rise of the oxygen sensor 26 may be restricted by the control on the supply power to the heater 33. Further, this control restricts degradation of the oxygen sensor 26 which will otherwise be promoted by the excessive temperature rise of the oxygen sensor 26.

In the present embodiment, not only the target impedance is repeatedly altered in accordance with deterioration of the oxygen sensor 26 but also abnormality determination of the oxygen sensor 26 is made. That is, the abnormality is determined when the heater is supplied with the power which corresponds to the operating limit of the oxygen sensor 26, thereby maintaining operation of the oxygen sensor 26. Further, when the deterioration progresses beyond an allowable limit, wasting of electric power is restricted.

In the present embodiment, because the abnormality determination is made only within the steady operating state (step 503 in FIG. 12), influence of the exhaust gas temperature on the heater supply power can be eliminated to provide a proper determination result.

Although the target impedance is altered stepwisely in the present embodiment, it may be altered linearly in correspondence with deterioration of the oxygen sensor 26.

Second Embodiment

Figure 13:
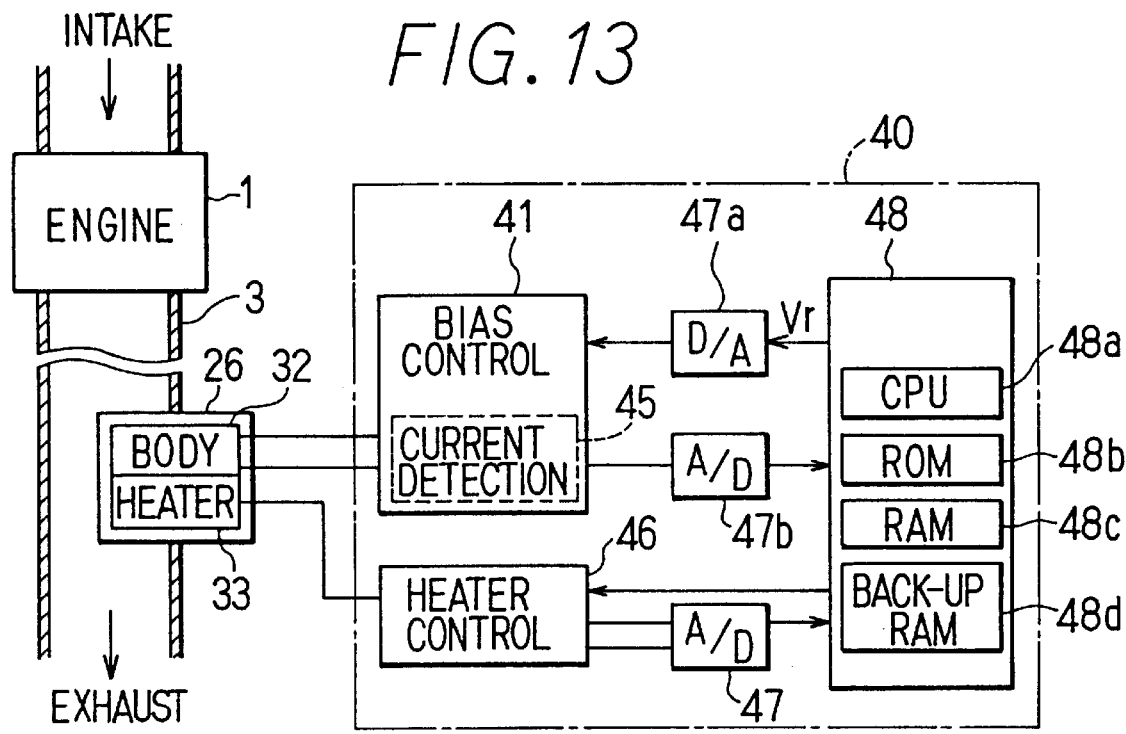
FIG. 13 is an electronic circuit diagram of ECU used in the second embodiment of the present invention.
Figure 14:
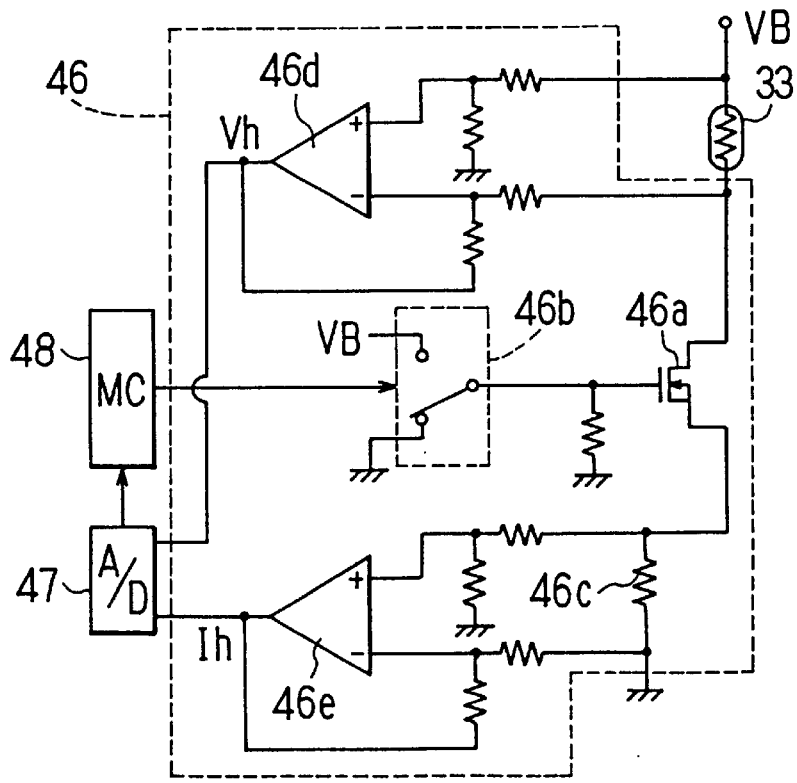
FIG. 14 is a circuit diagram of a heater control circuit.

In the second embodiment illustrated in FIG. 13, the circuit construction of ECU 40 connected to an oxygen sensor 26 having a heater 33 therein is different from the first embodiment in that a bias control circuit 41 includes a sensor current detection circuit 45 and is connected to a microcomputer (MC) 48 via a D/A converter 47b and an A/D converter 47b. A heater control circuit 46 is constructed as shown in FIG. 14. That is, the heater control circuit 46 includes a MOS transistor 46a connected between a switch 46b and the heater 33 so that the MOS transistor 46a controls power supply to the heater 33 in response to turning on and off of the switch 46b controlled by the microcomputer 48. The circuit 46 includes further an operational amplifier 46 connected to the heater 33 for providing a voltage (heater voltage Vh) across the heater 33, and an operational amplifier 46e connected to the heater through a resistor 46c for providing a voltage indicative of a current (heater current Ih) flowing through the heater 33. The microcomputer 48, receiving those detection values through an A/D converter 47, executes heater control in the following manner.

Figure 15:
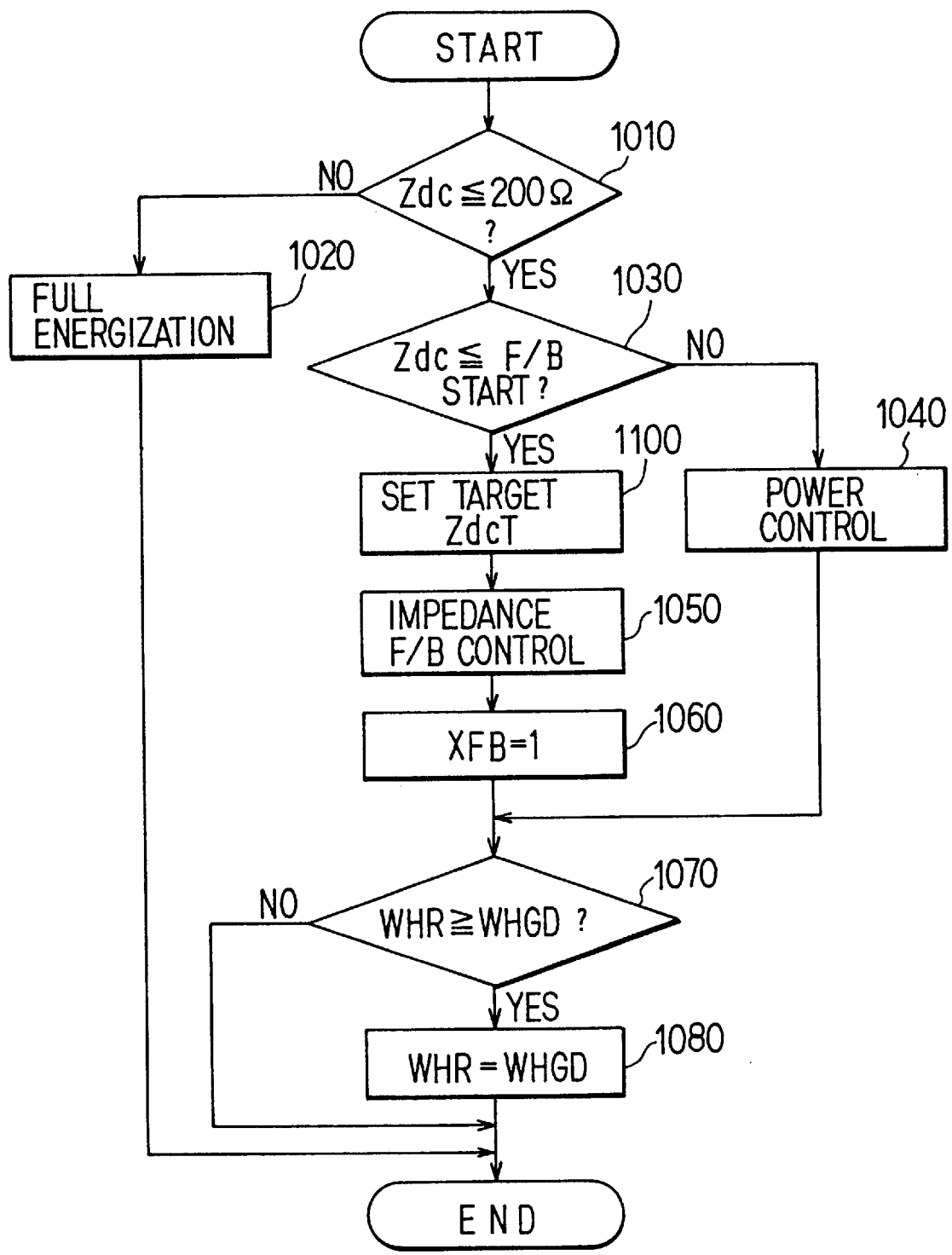
FIG. 15 is a flow chart illustrating a heater control routine.
Figure 18:
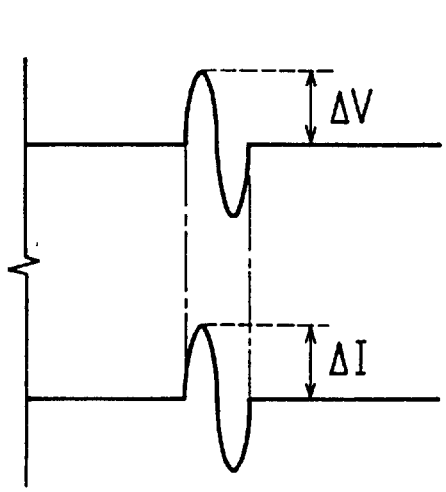
FIG. 18 is a time chart illustrating a sensor voltage and a sensor current for detecting an element impedance.

As illustrated in FIG. 15, the CPU 48a of the microcomputer 48 determines in step 1010 whether an element impedance Zdc is equal to or below a determination reference (200Ω) corresponding to a semi-activated condition of the sensor body. The element impedance Zdc in the present embodiment is detected, as shown in FIG. 18, by changing temporarily the voltage to the oxygen sensor 26 in positive and negative directions at the time of element impedance detection to cause changes in the current. The impedance Zdc is calculated by the CPU 48a as Zdc=ΔV/ΔI, wherein ΔV and ΔI correspond to the positive or negative changes in the sensor voltage and the sensor current, respectively. The impedance may be calculated alternatively by using both positive and negative changes or by using Zdc=Vneg/Ineg as in the first embodiment.

The CPU 48a makes negative determination (NO) when the element temperature is still low such as at cold engine starting, and proceeds to step 1020 to execute a full energization control. This 100% duty power supply continues until the element impedance Zdc is decreased to 200Ω or lower.

Figure 19:
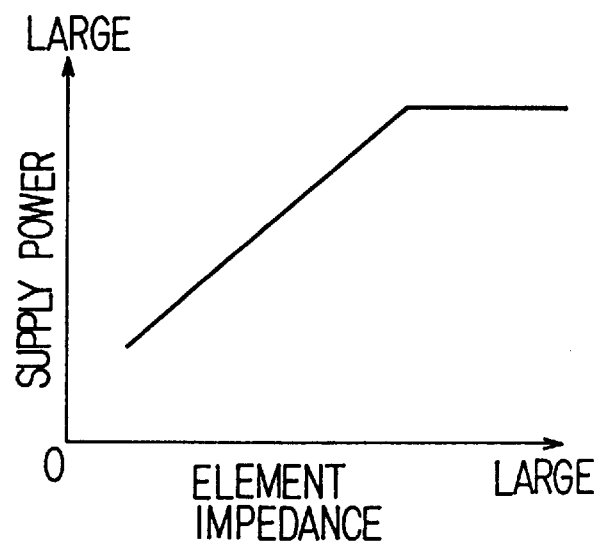
FIG. 19 is graph illustrating a mapped relation between an element impedance and a required supply power.

When the CPU 48a makes affirmative determination (YES) due to heating operation of the heater 33, it determines whether the impedance Zdc is equal to or lower than an impedance feedback control start reference which is set to correspond to the activation of the sensor 26 and to about ZdcT (target impedance)+10Ω. If the initial target impedance before sensor deterioration is 30Ω, the impedance feedback control start reference is set to 40Ω. If the determination is negative because of incompletion of the sensor activation, the CPU 48a proceeds to step 1040 to execute heater power control. That is, a required heater supply power is determined by the detected element impedance Zdc based on a predetermined relation illustrated in FIG. 19, and the power supply duty is calculated from the required heater supply power.

With the affirmative determination in step 1030, on the other hand, the CPU 48a proceeds from step 1030 to step 1100 to set the target element impedance ZdcT, and then to step 1050 to execute an element impedance feedback control. In this control, the control duty Duty is calculated as follows with i–1 representing previous calculation cycle. The CPU 48a also calculates a required supply power WHR in correspondence with the calculated duty Duty.

$$Duty = GP + GI + GD:$$

wherein $$GP = KP \cdot (Zdc - ZdcT),$$

$$GI = GIi{-}1 + KI \cdot (Zdc - ZdcT),$$

and $$GD = KD \cdot (Zdc - Zdci{-}1).$$

The CPU 48a, then setting a feedback execution flag XFB to 1 in step 1060, determines in step 1070 whether the calculated or required supply power WHR is equal to or above a predetermined maximum limit (i.e., supply power guard value) WHGD. If affirmative, i.e., the required supply power is too high, the CPU 48a limits the supply power WHR to the maximum limit WHGD in step 1080. Thus, the calculated duty Duty will also be limited to a limited duty corresponding to the maximum limit of the supply power. If WHR<WHGD, the CPU 48a ends this routine so that the heater 33 is supplied with the required supply power as calculated.

Figure 16:
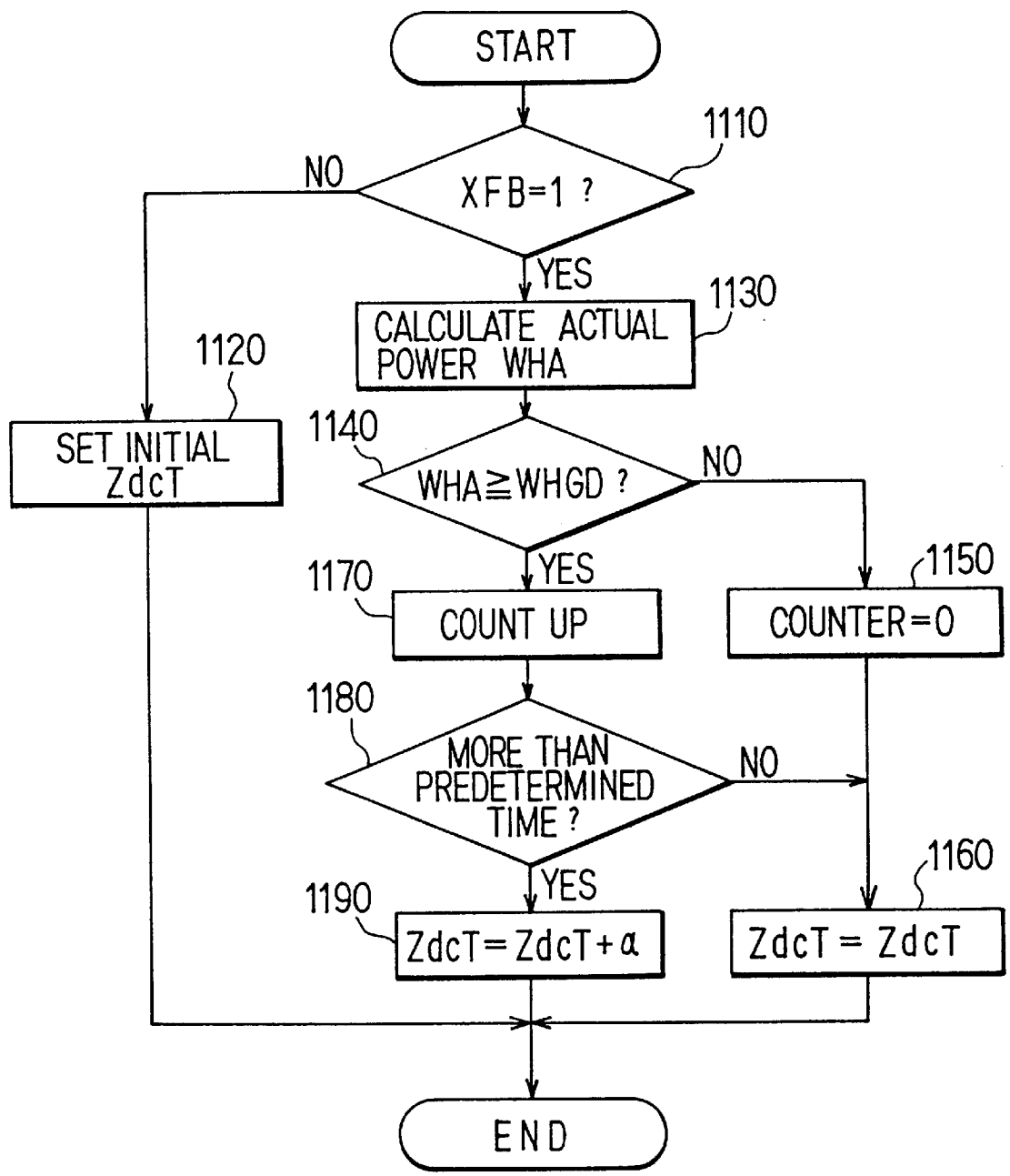
FIG. 16 is a flowchart illustrating a target impedance setting routine.

In the target impedance setting step 1100 in FIG. 15, as illustrated in detail in FIG. 16, the CPU 48a determines whether the impedance feedback flag XFB is 1. If XFB=0 indicating that no feedback is being executed, the CPU 48a reads in step 1120 the target impedance ZdcT from a back-up RAM 48d of the microcomputer 48 and set it as an initial target impedance, so that this initial impedance may be used at the time of starting the impedance feedback control of step 1050 in FIG. 15. If XFB=1 indicating that the impedance feedback control is being executed, on the other hand, the CPU 48a proceeds to step 1130 to calculate an actual heater supply power WHA from the detected heater voltage Vh and the heater current Ih, i.e., WHA=Vh·Ih.

The CPU 48a then compares in step 1140 the actual supply power WHA with the maximum limit WHGD. If NO (i.e., WHA<WHGD), the CPU 48a clears in step 1150 its counter which measures the time period of WHA≧WHGD and then in step 1160 maintains the target impedance ZdcT at that time so that this target impedance ZdcT is used in the impedance feedback control in FIG. 15.

If WHA≧WHGD in step 1140, the CPU 48a counts up the time of WHA≧WHGD in step 1170 and determines in step 1180 whether the measured time reaches a predetermined time (e.g., 5 minutes). With the affirmative determination, the CPU 48a increases in step 1190 the target impedance ZdcT by an increment α, i.e., from ZdcT to ZdcT+α. The target impedance ZdcT thus altered in step 1190 is stored in the back-up RAM 48d, which maintains its storage contents even after engine stop, so that the stored target impedance ZdcT may be read out in step 1120 when the heater control is executed next time again.

It will be understood in the above routines that the processing of the CPU 48a in the order of 1140, 1170, 1180 and 1190 means increase in the element impedance Zdc due to the sensor deterioration. If the impedance feedback control is continued with the initial target impedance unchanged, it is likely to cause the sensing element to be excessive heated. Therefore, the target impedance ZdcT is altered to protect the sensing element from overheating which will adversely deteriorates the sensing element.

Figure 17:
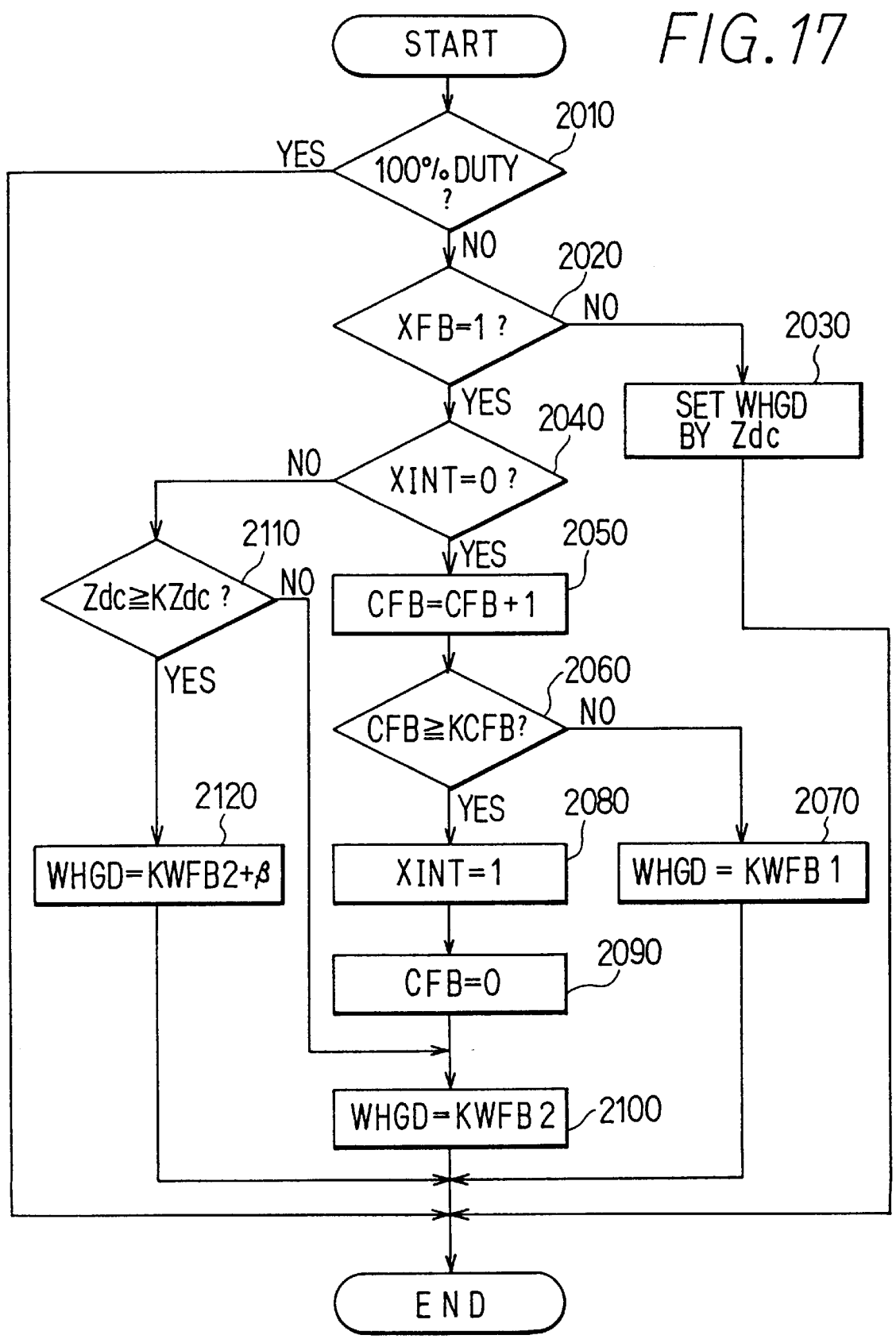
FIG. 17 is a flowchart illustrating a supply power limit setting routine.

The maximum limit (guard limit) WHGD of the supply power used in the foregoing routines (FIGS. 15 and 16) is determined by a setting routine illustrated in FIG. 17.

The CPU 48a first determines in step 2010 whether the heater 33 is being controlled with 100% duty. If YES, the routine ends without setting any limit WHGD.

If the determination is NO, however, the CPU 48a determines in step 2020 whether the impedance feedback control flag XFB is 1. If XFB=0 representing execution of the power control, the CPU 48a sets in step 2030 the maximum limit WHGD in accordance with the element impedance Zdc based on a predetermined relation illustrated in FIG. 20.

Figure 20:
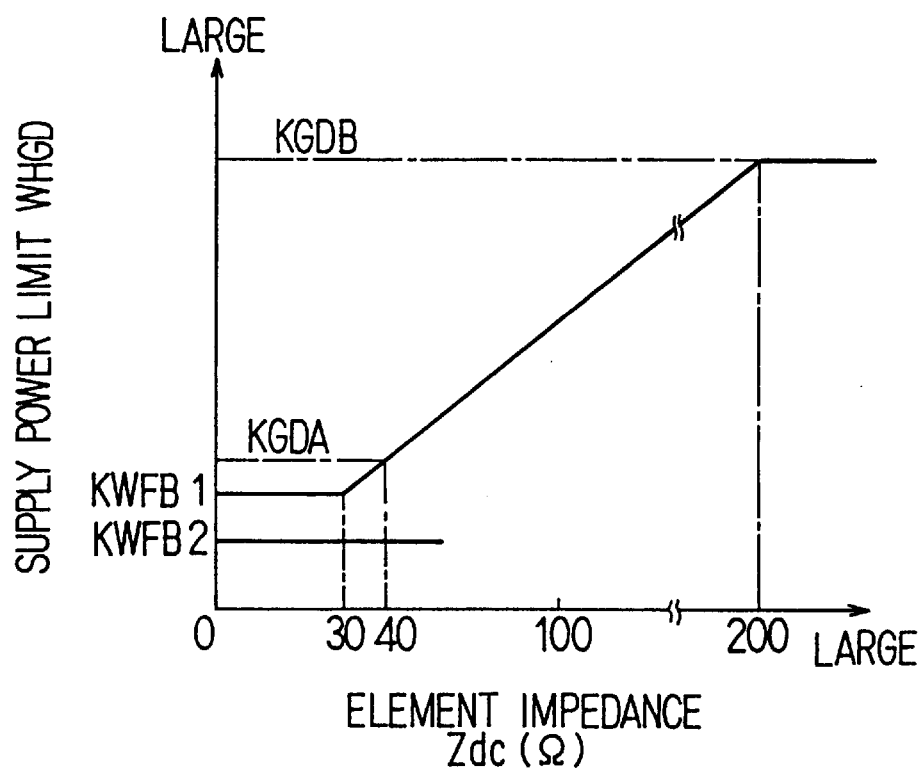
FIG. 20 is a graph illustrating a relation between an element impedance and a supply power limit.

In FIG. 20, the limit WHGD increases proportionally with the element impedance as long as the element impedance is within the range from Zdc=30Ω (initial target impedance for starting the impedance feedback control) to, while it is unchanged below 30Ω and above 200Ω. Therefore, when the power control is executed (40Ω<Zdc<200Ω and XFB=0), the limit WHGD is set between KGDA and KGDB. The relation in FIG. 20 is determined with the target impedance ZdcT being 30Ω. If the target impedance ZdcT is altered to be larger in the routine of FIG. 16, the maximum limit is also altered to be larger.

If XFB=1, the CPU 48a determines in step 2040 whether a limit setting flag XINT is 0. The flag XINT means that the limit WHGD has been set to the initial value after the start of heater control by the element impedance feedback control. Because XINT=0 initially, the CPU 48a increments a feedback start counter CFB in step 2050 and then determines whether the counter CFB has reached a predetermined value KCFB in step 2060. The predetermined value KCFB is set to correspond to a time period (e.g., 30 seconds) required to heat the oxygen sensor 26 uniformly after the cold state.

If CFB<KCFB, the CPU 48a proceeds to step 2070 to set the limit WHGD to KWFB1, which corresponds to the limit WHGD at the time of Zdc=30Ω (FIG. 20), and ends this routine. If CFB≧KCFB in step 2060, the CPU 48a sets the limit setting flag XINT=1 in step 2080 and clears the counter CFB to 0 in step 2090. The CPU 48a thereafter sets in step 2100 the limit WHGD to KWFB2 which corresponds to the normal value of the supply power limit after the sensor activation and is smaller than KWFB1 (FIG. 20).

Once the limit setting flag XINT has been set to 1 in step 2080, the CPU 48a repeats to make the negative determination in step 2040 and determines in step 2110 whether the element impedance Zdc is equal to or above a determination reference KZdc which is higher than the target impedance ZdcT altered as described above. The CPU 48a proceeds to step 2100 in response to the negative determination (Zdc<KZdc), while it proceeds to step 2120 in response to the affirmative determination (Zdc≧KZdc) to increase the limit WHGD to KWFB2+β.

Figure 21:
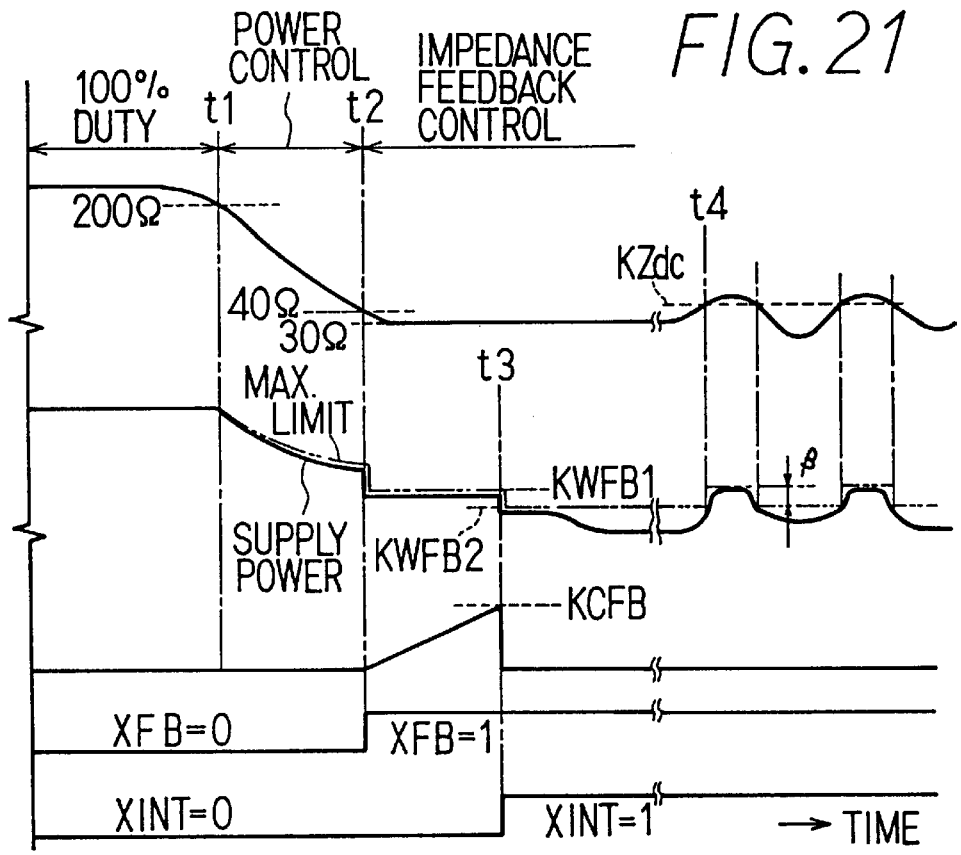
FIG. 21 is a time chart illustrating operation of the second embodiment.

The second embodiment operates in the manner illustrated in FIG. 21 in which it is assumed that the engine is started when the oxygen sensor 26 is still cold, i.e., the initial element impedance Zdc is above 200Ω.

At time t1 when the element impedance Zdc decreases to 200Ω, the power supply control to the heater 33 is changed from 100% duty power (step 1020 in FIG. 15) to the power control in which the heater supply power is controlled by the element impedance Zdc (step 1040 in FIG. 15). The limit WHGD is set in accordance with the element impedance as illustrated in FIG. 20 (step 2030 in FIG. 17).

When the element impedance Zdc decreases to the impedance feedback start reference (40Ω initially before sensor degradation) at time t2, the impedance feedback control starts and the feedback execution flag is set to 1 (steps 1050 and 1060 in FIG. 15). The maximum limit WHGD is set to KWFB1.

At this time t2, the feedback start counter CFB starts to count up. When the CFB value reaches the predetermined value KCFB at t3, the limit setting flag XINT is set to 1 and simultaneously the limit WHGD is altered from KWFB1 to KWFB2. The limit WHGD is maintained at KWFB2 thereafter. The actual heater supply power WHA gradually decreases as the sensor temperature rises. Once the element temperature reaches the activation temperature, the sensing element is maintained at around the activation temperature.

It may however happen that the element temperature will decrease to be lower than the activation temperature, when the exhaust gas temperature decreases rapidly at the time of engine transient operations such as fuel cut-off which will produce no mixture combustion heat. In this instance, as shown in FIG. 21, the element impedance Zdc will change with changes in the element temperature after time t4. That is, the impedance Zdc will increase as the element temperature decreases. When the element impedance Zdc rises above the reference KZdc, the limit WHGD is increased by the amount β. When the element impedance Zdc falls below the reference KZdc, the limit WHGD is returned to the KWFB2 again.

According to the present embodiment, the following advantages will be provided.

(a) As the heater supply power WH is limited by the maximum power limit WHGD, the heater supply power is provided stably and hence the excessive heating by the heater 33 is restricted even when the oxygen sensor 26 deteriorates or sensor environment such as engine exhaust gas temperature changes.

(b) As the maximum limit WHGD is set higher than normal until the oxygen sensor 26 is heated uniformly and not only locally (step 2070 in FIG. 17), activation of the oxygen sensor 26 from its cold state can be promoted. This is because the higher supply power provides more heat which will compensate for the dissipation of heat from the heater 33 to the surrounding low temperature areas.

(c) As the maximum limit WHGD is set in accordance with the element impedance Zdc (step 2030 in FIG. 17), the limit can be set appropriately even in the case the heater supply power is controlled in open-loop.

Figure 22:
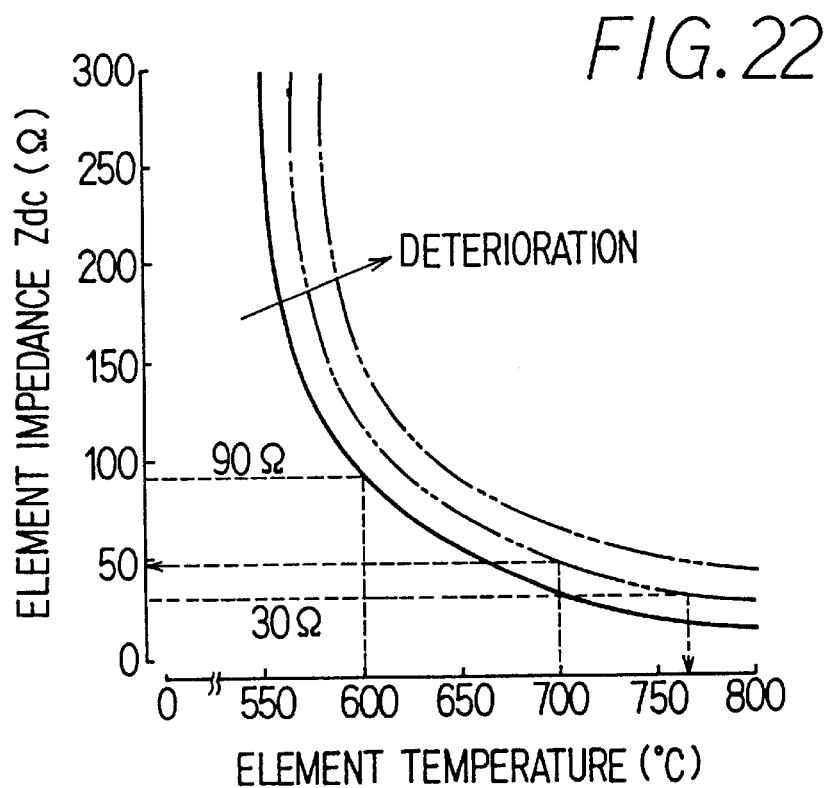
FIG. 22 is a graph illustrating a relation between an element impedance and an element temperature.

(d) During the element impedance feedback control, when it is determined that the actual heater supply power WHA is larger than the maximum limit WHGD for the predetermined period (step 1190 in FIG. 16), the target impedance ZdcT is increased (step 1190 in FIG. 16). As the oxygen sensor 26 deteriorates and its element impedance Zdc increases, it is likely that the supply power WH excessively increases and overheats the sensing element. As illustrated in FIG. 22, the sensor temperature may be maintained at the optimum activation temperature (700° C.) by setting the target impedance ZdcT to 30Ω before sensor deterioration. After the sensor deterioration, the same impedance feedback control will cause excessive element temperature rise. The element temperature will become higher as the oxygen sensor 26 deteriorates more. When the oxygen sensor 26 deteriorates, the element impedance Zdc increases and the actual heater supply power WH increases to the limit WHGD. If WH≧WHGD continues, it is determined that the oxygen sensor has deteriorated. Therefore, when the sensor deterioration is detected from the heater supply power, the element temperature can be maintained at the optimum activation temperature (700° C.) during the element impedance feedback control by altering the target impedance ZdcT to a higher value.

(e) At the time of altering or renewing the target impedance ZdcT, the new target impedance ZdcT is stored each time in the back-up RAM 48d so that the target impedance ZdcT need not be calculated in accordance with the sensor deterioration each time the engine is started. The excessive deterioration (abnormality) of the oxygen sensor 26 may be determined if the target impedance ZdcT is increased to a determination reference.

(f) When the element impedance Ztc exceeds the determination reference KZdc, the maximum limit WHGD against the heater supply power WH is increased by the amount β (step 212 in FIG. 17). Therefore, even when the engine rapidly decelerates and runs without fuel supply causing decrease in the temperature of the oxygen sensor 26 and the increase in the element impedance ZdcT, the heater supply power is supplied to the heater 33 to maintain activation and the response characteristics of the oxygen sensor 26.

The present embodiment may be modified as follows.

Although the maximum limit WHGD is switched from KWFB1 to KWFB2 depending on the elapse of time KCFB (step 2060) after the start of element impedance feedback control in the routine of FIG. 17, it may be changed gradually from KWFB1 to KWFB2. KWFB1 may be so set to vary in accordance with the time from engine starting to the starting of the element impedance feedback control. Preferably, KWFB1 is decreased to approach KWFB2 as the time becomes shorter. KWFB1 need not be set at the time of initial sensor heating.

Figure 23:
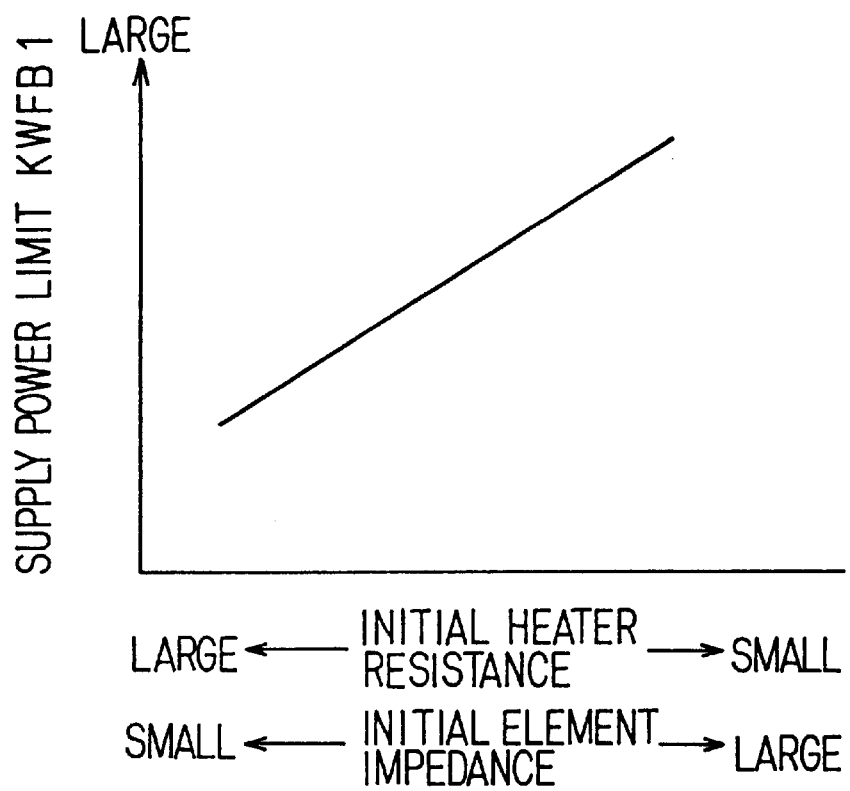
FIG. 23 is a graph illustrating a mapped relation between an initial heater resistance of impedance and a supply power limit.
Figure 24:
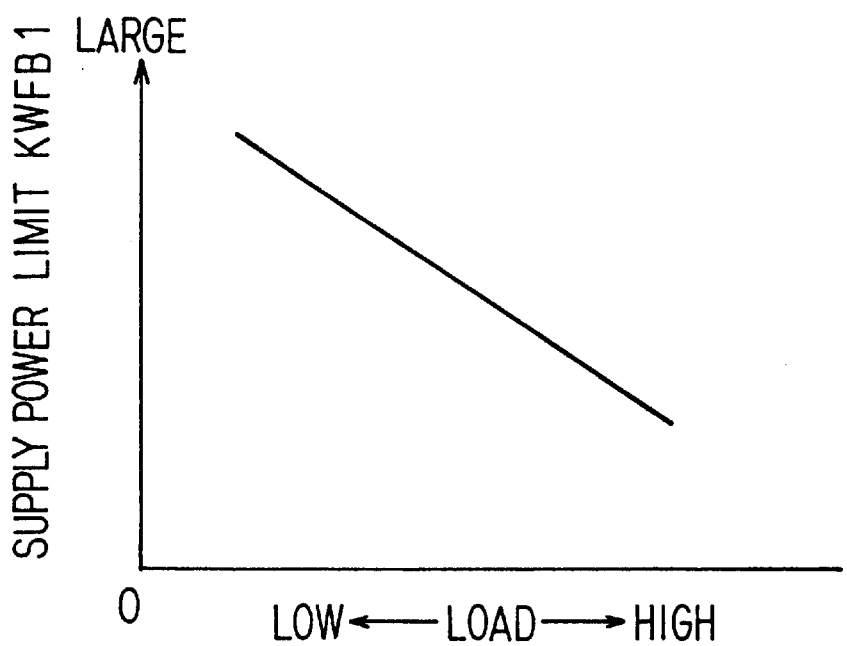
FIG. 24 is a graph illustrating a mapped relation between an engine load and a supply power limit.

The maximum limit KWFB1 at the time of starting the element impedance feedback control may be set by mapped data illustrated in FIGS. 23 and 24. That is, KWFB1 is increased as the initial heater resistance decreases or the initial element impedance increases (FIG. 23), while KWFB1 is decreased as the engine load increases (FIG. 24).

In the heater control, the element impedance feedback control after the sensor activation may be obviated and the power control having been executed until the sensor activation may be continued even after the sensor activation. In this instance, the overheating of the sensing element may be restricted by the use of maximum limit WHGD. As the element impedance corresponds to the element temperature, the maximum limit may be set in accordance with the element impedance.

Although the maximum limit WHGD is altered by the comparison of the element impedance Zdc with the determination reference KZdc (steps 2110 and 2120 in FIG. 17) so that decrease in the sensing element temperature caused mostly by the decrease in the exhaust gas temperature is compensated for, the maximum limit WHGD may be increased as exhaust gas temperature decreases.

The decrease in exhaust gas temperature may be detected directly from the exhaust gas temperature or indirectly from the time period of fuel supply cut-off.

The oxygen sensor may be another type which produces two voltage levels depending on the air-fuel mixture ratio richer or leaner than the stoichiometric ratio.

While the present invention has been described with reference to what are presently considered to be preferred embodiments thereof, it is to be understood that the invention is not limited to the disclosed embodiments. To the contrary, the invention is intended to cover various modifications and equivalent arrangements included within the spirit and scope of the appended claims.

What is claimed is:

1. An oxygen sensor heating control apparatus comprising:

an oxygen sensor having a sensing element for outputting current proportional to oxygen concentration, and a heater for heating the sensing element;

element impedance detecting means for detecting impedance of the sensing element;

heater supply power control means for feedback-controlling supply power to the heater thereby to maintain the element impedance detected by the element impedance detecting means at a target impedance;

deterioration determining means for determining deterioration which causes increase in internal impedance of the sensing element; and target impedance altering means for altering the target impedance in response to a determination of the deterioration.

2. An oxygen sensor heating control apparatus comprising:

an oxygen sensor having a sensing element for outputting current proportional to oxygen concentration, and a heater for heating the sensing element;

element impedance detecting means for detecting impedance of the sensing element;

heater supply power control means for feedback-controlling supply power to the heater thereby to maintain the element impedance detected by the element impedance detecting means at a target impedance;

heater supply power detecting means for detecting heater supply power;

heater supply power comparing means for comparing the detected heater supply power with a predetermined determination reference; and target impedance altering means for altering the target impedance in response to a comparison result of the heater supply power comparing means indicating that the heater supply power is above the predetermined determination reference.

3. An oxygen sensor heating control apparatus according to claim 2, wherein:

the heater supply power comparing means includes first comparing means for comparing the heater supply power with a first determination reference, and a second comparing means for comparing the heater supply power with a second determination reference larger than the first determination reference; and the target impedance altering means increases the target impedance to a first target impedance in response to a comparison result of the first comparing means indicating that the heater supply power reaches the first determination reference, and to a second target impedance larger than the first determination reference in response to a comparison result of the second comparing means indicating that the heater supply power reaches the second determination reference.

4. An oxygen sensor heating control apparatus according to claim 2, further comprising:

sensor abnormality determining means for determining abnormality of the oxygen sensor when the heater supply power exceeds an abnormality determination reference larger than the predetermined determination reference.

5. An oxygen sensor heating control apparatus according to claim 2, further comprising:

operating state detecting means for detecting operating state of an engine; and initiating means for initiating, when the detected operating state enters into a steady state, control operation by the heater supply power comparing means and impedance altering operation of the target impedance altering means.

6. An oxygen sensor heating control apparatus comprising:

an oxygen sensor having a sensing element for outputting current proportional to oxygen concentration, and a heater for heating the sensing element;

element impedance detecting means for detecting impedance of the sensing element;

heater supply power control means for feedback-controlling supply power to the heater thereby to maintain the element impedance detected by the element impedance detecting means at a target impedance;

heater supply power detecting means for detecting heater supply power; and target impedance setting means for setting the target impedance so that the target impedance increases as the detected heater supply power increases.

7. An oxygen sensor heating control method comprising the steps of:

detecting an internal impedance of a sensing element of an oxygen sensor;

heating the sensing element by a heater to attain a target impedance;

determining deterioration of the oxygen sensor based on the detected internal impedance of the sensing element; and altering the target impedance increasingly in response to the determined deterioration of the oxygen sensor.

8. An oxygen sensor heating control method according to claim 7, wherein:

the deterioration determining step compares supply power to the heater with a deterioration determination reference; and the target impedance altering step increases the target impedance when the supply power reaches the determination reference.

9. An oxygen sensor heating control method according to claim 8, further comprising the steps of:

determining abnormality of the oxygen sensor by comparing the supply power to the heater with an abnormality determination reference higher than the deterioration determination reference; and disabling the impedance altering step when the supply power reaches the abnormality determination reference.

10. An oxygen sensor heating control method according to claim 8, wherein:

the deterioration determining step compares the supply power to the heater with a plurality of deterioration determination references; and the target impedance altering step increases the target impedance to a higher one as the supply power reaches higher one of the determination references.

* * * * *

UNITED STATES PATENT AND TRADEMARK OFFICE

CERTIFICATE OF CORRECTION

PATENT NO. : 5,974,857
DATED : November 2, 1999
INVENTOR(S) : YAMASHITA et al

It is certified that error appears in the above-identified patent and that said letters patent is hereby corrected as shown below:

Front page  75] should read:

--Inventors: Yukihiro Yamashita; Hisashi Iida. Both of Kariya Japan--

Signed and Sealed this

Third Day of April, 2001

*Attest:*

NICHOLAS P. GODICI

*Attesting Officer*  Acting Director of the United States Patent and Trademark Office